United States Patent [19]

Markwell et al.

[11] Patent Number: 4,833,136
[45] Date of Patent: May 23, 1989

[54] PHARMACEUTICALLY USEFUL PYRAZOLO[4,3-B]PYRIDINES

[75] Inventors: Roger E. Markwell; Robert W. Ward; Carol R. De Mello, all of Harlow, England

[73] Assignee: Beecham Group p.l.c., Brentford, England

[21] Appl. No.: 8,267

[22] Filed: Jan. 29, 1987

[30] Foreign Application Priority Data

Jan. 30, 1986 [GB] United Kingdom ............... 8602236
Apr. 11, 1986 [GB] United Kingdom ............... 8608918

[51] Int. Cl.$^4$ .................... A61K 31/44; C07D 471/04
[52] U.S. Cl. .................................. 514/212; 514/293; 514/303; 546/82; 546/119; 546/120; 540/597
[58] Field of Search ............ 546/82, 119, 120; 540/597; 514/212, 293, 303

[56]  References Cited

U.S. PATENT DOCUMENTS

| 4,559,348 | 12/1985 | Hurst et al. | 546/119 |
| 4,576,952 | 3/1986 | Hurst et al. | 546/119 |
| 4,621,089 | 11/1986 | Ward et al. | 546/120 |
| 4,670,432 | 6/1987 | Ward et al. | |

FOREIGN PATENT DOCUMENTS

| 119774 | 9/1984 | European Pat. Off. | 471/04 |
| 151962 | 8/1985 | European Pat. Off. | 471/04 |
| 152910 | 8/1985 | European Pat. Off. | 471/04 |
| 154220 | 9/1985 | European Pat. Off. | 471/04 |
| 52-077086 | 6/1977 | Japan | |

OTHER PUBLICATIONS

*Chemical Abstracts*, 87, 578, Abstract 168030e (6/29/77)
*Journal of Heterocyclic Chemistry*, 8(6), 1035-37 (Dec. 1971).

Primary Examiner—Mary C. Lee
Assistant Examiner—Bernard I. Dentz
Attorney, Agent, or Firm—James F. Haley, Jr.; David K. Barr

[57] ABSTRACT

A compound of the formula (I) or a salt or solvate thereof:

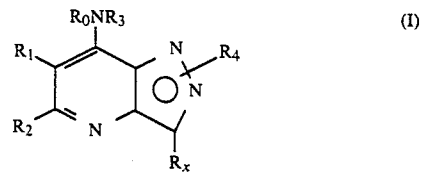

in which:

$R_0$ is hydrogen or $C_{1-6}$ alkyl; or together with $R_3$ is $C_{4-6}$ polymethylene;

$R_1$ and $R_2$ are both hydrogen; or $R_1$ is hydrogen, $C_{1-6}$ alkyl; and $R_2$ is CN; $CR_5R_6Y$ where $R_5$ and $R_6$ are independently selected from hydrogen and $C_{1-4}$ alkyl and Y is selected from hydrogen, $OR_7$ or $SR_7$ where $R_7$ is hydrogen, $C_{1-4}$ alkyl or $C_{2-4}$ alkanoyl, and $NR_8R_9$ where $R_8$ and $R_9$ are independently hydrogen, $C_{1-4}$ alkyl, $C_{2-4}$ alkenyl or $C_{2-4}$ alkanoyl or together are $C_{4-6}$ polymethylene; or $COR_{10}$ where $R_{10}$ is OH or $C_{1-4}$ alkyl, or $COR_{10}$ is a pharmaceutically acceptable ester or amide, or $R_2$ is hydrogen, $C_{1-6}$ alkyl, or phenyl optionally substituted by halogen, $CF_3$, $C_{1-4}$ alkoxy or $C_{1-4}$ alkyl, and $R_1$ is CN, $CR_5R_6Y$ or $COR_{10}$ as defined for $R_2$ above; or $R_1$ and $R_2$ together form $C_3$-$C_6$ polymethylene optionally substituted by $C_1$-$C_4$ alkyl;

$R_3$ is hydrogen; or $C_{1-10}$ alkyl or $C_{3-10}$ cycloalkyl, either optionally substituted by hydroxy, $C_{1-4}$ alkoxy, thiol, $C_{1-4}$ alkylthio or $NR_{11}R_{12}$ wherein $R_{11}$ and $R_{12}$ are independently hydrogen, $C_{1-6}$ alkyl or $C_{2-7}$ alkanoyl or together are $C_{3-6}$ polymethylene; $C_{2-10}$ alkenyl; or phenyl optionally substituted by one or two of halogen, $CF_3$, $C_{1-4}$ alkoxy, $C_{1-4}$ alkyl, hydroxy, nitro, cyano, $C_{2-10}$ acyloxy, $NR_{13}R_{14}$ wherein $R_{13}$ and $R_{14}$ are independently selected from hydrogen, $C_{1-6}$ alkyl, or $C_{2-7}$ alkanoyl; or $COR_{15}$ wherein $R_{15}$ is hydroxy, $C_{1-6}$ alkoxy or $NR_{16}R_{17}$ wherein $R_{16}$ and $R_{17}$ are independently selected from hydrogen or $C_{1-6}$ alkyl; or $R_3$ is a mono- or fused bi-cyclic heteroaryl group having up to ten atoms in the aromatic ring(s), not more than two of which are selected from nitrogen, oxygen or sulphur, other than those containing basic nitrogen, optionally substituted by one or two substituents selected from halogen, $CF_3$, $C_{1-4}$ alkoxy, $C_{1-4}$ alkyl, hydroxy, nitro, cyano, $C_{2-10}$ acyloxy, $NR_{23}R_{24}$ wherein $R_{23}$ and $R_{24}$ are independently selected from hydrogen, $C_{1-6}$ alkyl, $C_{2-7}$ alkanoyl or $C_{1-6}$ alkylsulphonyl; or $COR_{25}$ wherein $R_{25}$ is hydroxy, $C_{1-6}$ alkoxy or $NR_{26}R_{27}$ wherein $R_{26}$ and $R_{27}$ are independently selected from hydrogen or $C_{1-6}$ alkyl;

$R_4$ is hydrogen, or $C_{1-4}$ alkyl, phenyl or benzyl, each of which is optionally substituted in the phenyl ring by one or two of halogen, $CF_3$, $C_{1-4}$ alkoxy or $C_{1-4}$ alkyl and is attached at nitrogen atom 1 or 2; and $R_x$ is $C_{1-6}$ alkyl, halogen, nitro, $NR_{18}R_{19}$ where $R_{18}$ and $R_{19}$ are independently hydrogen, $C_{1-6}$ alkyl or $C_{2-7}$ alkanoyl, nitrile, COOH, $CONH_2$; phenyl or benzyl optionally substituted by one or two of halogen, nitro, $C_{1-6}$ alkoxy, hydroxy, $C_{2-7}$ alkanoyloxy, $NR_{18}R_{19}$, $C_{1-6}$ alkyl, $CF_3$, CN; thienyl, furyl or pyrryl optionally N-substituted by $C_{1-6}$ alkyl, with the proviso that $R_0$ and $R_3$ are not both hydrogen when $R_1$ is hydrogen and $R_2$ and $R_x$ are methyl, is useful for treating inflammatory or allergic conditions.

10 Claims, No Drawings

PHARMACEUTICALLY USEFUL PYRAZOLO[4,3-B]PYRIDINES

The present invention relates to pyrazolopyridines having useful pharmacological activity, to a process for their preparation and to their use as anti-inflammatories.

J. Heterocycl. Chem. 1971, 8(6), 1035-7 discloses compounds of the formula (A):

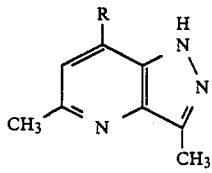

wherein R is $NH_2$, OH $NAc_2$ or Cl. The compound wherein R is $NAc_2$ is described as having CNS antidepressant activity in mice.

Japanese Published (Kokai) Patent Application No. 52-077086 discloses compounds of the formula (B):

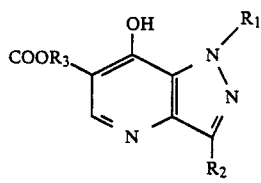

wherein $R_1$ is hydrogen, lower alkyl or phenyl, $R_2$ is hydrogen or lower alkyl and $R_3$ is lower alkyl. These compounds are described as having anti-inflammatory and anti-bacterial properties.

A further group of pyrazolopyridine derivatives has now been discovered that have anti-inflammatory (including anti-rheumatic) and/or anti-allergy activity.

Accordingly, the present invention provides a compound of the formula (I) or a salt or solvate thereof:

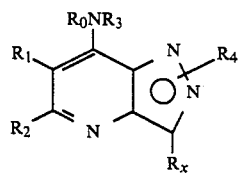

in which:

$R_0$ is hydrogen or $C_{1-6}$ alkyl; or together with $R_3$ is $C_{4-6}$ polymethylene;

$R_1$ and $R_2$ are both hydrogen, or $R_1$ is hydrogen, $C_{1-6}$ alkyl; and $R_2$ is CN; $CR_5R_6Y$ where $R_5$ and $R_6$ are independently selected from hydrogen and $C_{1-4}$ alkyl and Y is selected from hydrogen, $OR_7$ or $SR_7$ where $R_7$ is hydrogen, $C_{1-4}$ alkyl or $C_{2-4}$ alkanoyl, and $NR_8R_9$ where $R_8$ and $R_9$ are independently hydrogen, $C_{1-4}$ alkyl, $C_{2-4}$ alkenyl or $C_{2-4}$ alkanoyl or together are $C_{4-6}$ polymethylene; or $COR_{10}$ where $R_{10}$ is OH or $C_{1-4}$ alkyl, or $COR_{10}$ is a pharmaceutically acceptable ester or amide, or $R_2$ is hydrogen, $C_{1-6}$ alkyl, or phenyl optionally substituted by halogen, $CF_3$, $C_{1-4}$ alkoxy or $C_{1-4}$ alkyl; and $R_1$ is CN, $CR_5R_6Y$ or $COR_{10}$ as defined for $R_2$ above; or $R_1$ and $R_2$ together form $C_3$-$C_6$ polymethylene optionally substituted by $C_1$-$C_4$ alkyl;

$R_3$ is hydrogen; or $C_{1-10}$ alkyl or $C_{3-10}$ cycloalkyl, either optionally substituted by hydroxy, $C_{1-4}$ alkoxy, thiol, $C_{1-4}$ alkylthio or $NR_{11}R_{12}$ wherein $R_{11}$ and $R_{12}$ are independently hydrogen, $C_{1-6}$ alkyl or $C_{2-7}$ alkanoyl or together are $C_{3-6}$ polymethylene; $C_{2-10}$ alkenyl; or phenyl optionally substituted by one or two of halogen, $CF_3$, $C_{1-4}$ alkoxy, $C_{1-4}$ alkyl, hydroxy, nitro, cyano, $C_{2-10}$ acyloxy, $NR_{13}R_{14}$ wherein $R_{13}$ and $R_{14}$ are independently selected from hydrogen, $C_{1-6}$ alkyl, or $C_{2-7}$ alkanoyl; or $COR_{15}$ wherein $R_{15}$ is hydroxy, $C_{1-6}$ alkoxy or $NR_{16}R_{17}$ where $R_{16}$ and $R_{17}$ are independently selected from hydrogen or $C_{1-6}$ alkyl; or $R_3$ is a mono- or fused bi-cyclic heteroaryl group having up to ten atoms in the aromatic ring(s), not mre than two of which are selected from nitrogen, oxygen or sulphur, other than those containing basic nitrogen, optionally substituted by one or two substituents selected from halogen, $CF_3$, $C_{1-4}$ alkoxy, $C_{1-4}$ alkyl, hydroxy, nitro, cyano, $C_{2-10}$ acyloxy, $NR_{23}R_{24}$ wherein $R_{23}$ and $R_{24}$ are independently selected from hydrogen, $C_{1-6}$ alkyl, $C_{2-7}$ alkanoyl or $C_{1-6}$ alkylsulphonyl; or $COR_{25}$ wherein $R_{25}$ is hydroxy, $C_{1-6}$ alkoxy or $NR_{26}R_{27}$ wherein $R_{26}$ and $R_{27}$ are independently selected from hydrogen or $C_{1-6}$ alkyl;

$R_4$ is hydrogen; or $C_{1-4}$ alkyl, phenyl or benzyl, each of which is optionally substituted in the phenyl ring by one or two of halogen, $CF_3$, $C_{1-4}$ alkoxy or $C_{1-4}$ alkyl and is attached at nitrogen atom 1 or 2; and $R_x$ is $C_{1-6}$ alkyl, halogen, nitro, $NR_{18}R_{19}$ where $R_{18}$ and $R_{19}$ are independently hydrogen, $C_{1-6}$ alkyl or $C_{2-7}$ alkanoyl, nitrile, COOH, $CONH_2$; phenyl or benzyl optionally substituted by one or two of halogen, nitro, $C_{1-6}$ alkoxy, hydroxy, $C_{2-7}$ alkanoyloxy, $NR_{18}R_{19}$, $C_{1-6}$ alkyl, $CF_3$, CN; thienyl, furyl or pyrryl optionally N-substituted by $C_{1-6}$ alkyl, with the proviso that $R_0$ and $R_3$ are not both hydrogen when $R_1$ is hydrogen and $R_2$ and $R_x$ are methyl.

Suitable values for $R_0$ include hydrogen, methyl, ethyl, n- and iso-propyl, preferably hydrogen.

Suitable values for $R_1/R_2$ include hydrogen, methyl, aminomethyl optionally N-substituted, and acetamidomethyl, or together forming $C_3$ or $C_4$ polymethylene.

Suitable values for $R_3$ include hydrogen; methyl, ethyl, n- and iso-propyl, n-, iso- sec- and tert-butyl, n-pentyl, $(CH_2)_nCH_3$ wherein n is 4 to 7, or cyclohexyl, optionally substituted by methyl, ethyl and/or hydroxy, methoxy, n- or iso-propoxy, thiol, methylthio or amino optionally substituted by one or two methyl or acetyl groups or by $C_4$ or $C_5$ polymethylene; prop-1-enyl, prop-2-enyl, 1-methylvinyl, but-1-enyl, but-2-enyl, but-3-enyl, 1-methylenepropyl, 1-methylprop-1-enyl and 1-methylprop-2-enyl in their E and Z forms where stereoisomerism exists; or phenyl optionally substituted by one or two chloro, bromo, methoxy, ethoxy, n- and iso-propoxy, methyl, ethyl, n- and iso-propyl, n-, iso-, sec- and tert-butyl, hydroxy, nitro, cyano, acetoxy, propionyloxy, benzyloxy, $NR_{13}{}^1R_{14}{}^1$ wherein $R_{13}{}^1$ and $R_{14}{}^1$ are independently selected from hydrogen, methyl, ethyl, n- and iso-propyl, acetyl, and propionyl; $COR_{15}{}^1$ wherein $R_{15}{}^1$ is hydroxy, methoxy, ethoxy or $NR_{16}{}^1R_{17}{}^1$ wherein $R_{16}{}^1$ and $R_{17}{}^1$ are independently selected from hydrogen, methyl, n- and iso-propyl. More suitable values for $R_3$ include n-butyl, iso-butyl, n-pentyl, prop-2-enyl, 2-methylallyl, 2-hydroxyethyl, 3-hydroxypropyl, 2-dimethylaminoethyl, 3-dimethylaminopropyl, 3-diethylaminopropyl, phenyl and phenyl substituted by one of hydroxy, nitro, cyano, carboxy, t-butyl and ethoxycarbonyl in the 3- or 4-position. Favourable values for $R_3$ include n-butyl, prop-2-enyl and 2-hydroxyethyl, 3-dimethylaminopropyl and 3-diethylaminopropyl.

When heteroaryl, suitable values for $R_3$ include furyl, thienyl, pyrryl, benzofuranyl, benzothienyl and indolyl optionally substituted by one or two chloro, bromo methoxy, ethoxy, n- and iso-propoxy, methyl, ethyl, n- and iso-propyl, n-, iso-, sec- tert-butyl, hydroxy, nitro, cyano, acetoxy, propionyloxy, benzyloxy, $NR_{23}{}^1 R_{24}{}^1$ wherein $R_{23}{}^1$ and $R_{24}{}^1$ are independently selected from hydrogen, methyl, ethyl, n- and iso-propyl, acetyl, propionyl; $COR_{25}{}^1$ wherein $R_{25}{}^1$ is hydroxy, methoxy, ethoxy or $NR_{26}{}^1 R_{27}{}^1$ wherein $R_{26}{}^1$ and $R_{27}{}^1$ are independently selected from hydrogen, methyl, n- and iso-propyl.

Suitable values for $R_x$ include chloro, bromo, methyl, thienyl, phenyl, and phenyl substituted with chloro, hydroxy or methoxy.

Suitable values for $R_{10}$ when $R_1/R_2$ is $COR_{10}$ and $COR_{10}$ is a pharmaceutically acceptable ester or amide include $C_{1-6}$ alkoxy, $C_{2-6}$ alkenyloxy, phenoxy or benzyloxy where the phenyl/benzyl ring is optionally substituted by one or two of halogen, $CF_3$, $C_{1-4}$ alkoxy and $C_{1-4}$ alkyl; or $R_{10}$ is $NOR_{20}R_{21}$ where $R_{20}$ and $R_{21}$ are independently hydrogen, $C_{1-6}$ alkyl, $C_{2-6}$ alkenyl, benzyl or phenyl optionally substituted as described above.

It will be appreciated that when $R_4$ is hydrogen the compounds of formula (I) exist as tautomers, i.e. the $R_4$ hydrogen atom is labile. The compounds wherein $R_4$ is hydrogen are therefore of formulae (IIa) and (IIb).

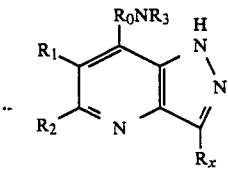

(IIa)

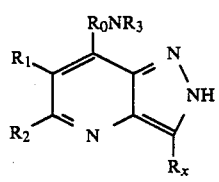

(IIb)

The compounds of the formula (I) can form acid addition salts with acids, such as the conventional pharmaceutically acceptable acids, for example hydrochloric, hydrobromic, phosphoric, acetic, fumaric, salicylic, citric, lactic, mandelic, tartaric and methanesulphonic. Such compounds form part of the present invention, as do solvates, for example hydrates, of the compounds of formula (I) or salts thereof.

There is a group of compounds wherein formula (I) of formula (III):

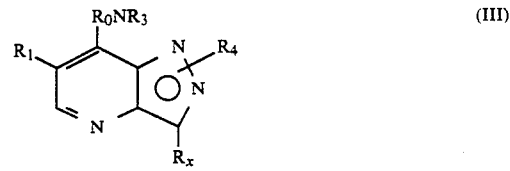

(III)

A further group of compounds within formula (I) is of formula (IV):

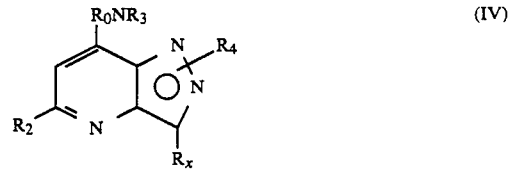

(IV)

Another group of compounds within formula (I) is of formula (V):

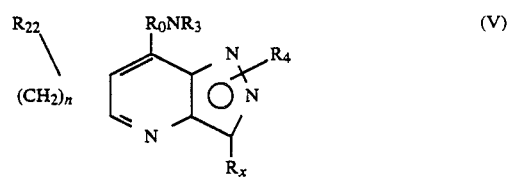

(V)

in which n is 3 to 5 and $R_{22}$ is hydrogen or $C_1$–$C_4$ alkyl.

In formula (III), (IV) and (V), $R_0$, $R_1$, $R_2$, $R_3$, $R_4$ and $R_x$, and suitable and preferred values for these variables, are as described for formula (I).

In a favored group of compounds within formula (I)
$R_0=H$,
$R_1=$Methyl when $R_2=H$, or
$R_2=H$ or methyl when $R_1=H$, or
$R_1$ and $R_2$ together form cyclohexano,
$R_3=$4-hydroxyphenyl, allyl, n-butyl, isobutyl, 2-hydroxyethyl, 3-hydroxypropyl, 3-dimethyl aminopropyl, or 3-diethylaminopropyl,
$R_4=$H or 2-Methyl, and
$R_x=$Methyl, phenyl, or 4-chlorophenyl.

The present invention also provides a process for the preparation of a compound of formula (I) or a salt or solvate thereof, which process comprises the reaction of a compound of formula (VI):

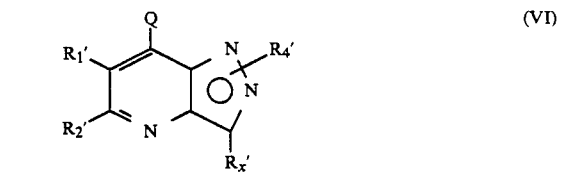

(VI)

wherein q is a leaving group $R_1{}'$, $R_2{}'$, $R_4{}'$ are $R_1$, $R_2$, $R_4$ and $R_x$ or groups or atoms convertible thereto, with a compound of formula (VII):

$HNR_0{}'R_3{}'$     (VII)

wherein $R_0{}'$ and $R_3{}'$ are $R_0$ and $R_3$ as defined for formula (I) or groups or atoms convertible thereto, to obtain a compound of formula (Ia)

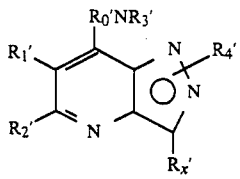

(Ia)

and then performing one or more of the following steps:

(a) when one or more of $R_0'$, $R_1'$, $R_2'$, $R_3'$, $R_4'$ or $R_x'$ are not $R_0$, $R_1$, $R_2$, $R_3$, $R_4$ or $R_x$ respectively, converting said one or more substituents to $R_0$, $R_1$, $R_2$, $R_3$, $R_3$, $R_4$ or $R_x$, to obtain a compound of formula (I)

(b) when $R_0'$, $R_1'$, $R_2'$, $R_3'$, $R_4'$ and $R_x'$ are $R_0$, $R_1$, $R_2$, $R_3$, $R_4$ and $R_x$, converting one or more of $R_0$, $R_1$, $R_2$, $R_3$, $R_4$ and $R_x$ to another $R_0$, $R_1$, $R_2$, $R_3$, $R_4$ or $R_x$, to obtain a compound of formula (I);

(c) forming a salt and/or solvate of the obtained compound of formula (I).

It will be appreciated that a compound of formula (Ia), or another compound of formula (I), may be converted to a compound of formula (I) by interconversion of suitable substituents. Thus certain compounds of formula (I) are useful intermediates in forming other compounds of the present invention.

Salts or solvates of the compounds of formula (I) are preferably pharmaceutically acceptable, but those which are not pharmaceutically acceptable may be useful as intermediates in the production of pharmaceutically acceptable salts or solvates. Accordingly such salts or solvates also form part of this invention.

Suitable leaving groups Q include halogens such as chloro and bromo, preferably chloro.

The reaction may be carried out under conventional conditions for nucleophilic aromatic displacements, at elevated temperatures using excess of reagent as solvent or in an inert solvent such as toluene, ethanol, dimethylformamide, dimethylsulphoxide, dioxan or water. However, when $R_3$ is a heterocycle, then $R_3'$ is advantageously a carboxylated heterocycle $R_3$ which decarboxylates in situ during reaction of compounds (VI) and (VII). In such a situation it is preferable that the reaction takes place in the presence of acetic acid, in addition to any inert solvent that is used.

The reaction preferably takes place in a sealed tube or pressure vessel if the compound of formula (VII) is of low boiling point.

Conversion of an $R_0$ hydrogen to an $R_0$ $C_{1-6}$ alkyl group may be carried out by conventional amine alkylation (with protection of $R_4$ if hydrogen) or acylation (e.g. formylation) followed by reduction.

Conversion of $R_1'/R_2'$ to $R_1/R_2$ may be carried out by conventional functional group interchanges. Thus for example:

(i) a CN group may be provided by the dehydration of an amide group, preferably with phosphorous pentoxide.

(ii) an hydroxymethyl group may be provided by the reduction of an alkoxycarbonyl group, preferably with a methyl hydride, such as LiAlH$_4$. In this case it is necessary to protect the pyrazole N-H with a suitable protecting group, such as 2-methoxy-2-propyl.

(iii) an alkanoyl group may be provided by the reaction of a CN group with an organo-metallic reagent such as a Grignard reagent.

(iv) a secondary alcohol group may be provided by the reduction of an alkanoyl group, preferably with a metal hydride.

(v) a tertiary alcohol group may be provided by the reaction of an alkanoyl group with an organo-metallic reagent such as a Grignard reagent.

(vi) a primary aminomethyl group may be provided by the reduction of a CN group, preferably with a metal hydride or using PtO$_2$/HCl-H$_2$.

(vii) an aminomethyl group may be provided by the reduction of the corresponding amide, preferably with a metal hydride.

(viii) an alkanoyloxyalkyl group may be provided by the acylation of the corresponding alcohol, preferably using the appropriate acid anhydride in trifluoroacetic acid at elevated temperatures.

(ix) an alkanoylaminoalkyl group may be provided by the acylation of the corresponding amino alkyl group, preferably using the appropriate acid anhydride under mild conditions.

(x) a methyl group in particular in the 6-position may be provided by the reduction of an alkoxycarbonyl group, preferably with lithium aluminium hydride.

(xi) an aminoalkyl group may be provided by converting the hydroxy of the corresponding alcohol to a leaving group and reacting with an appropriate amine, preferably a primary or secondary amine.

(xii) alternatively an aminoalkyl group of the formula $CH(R_5)NR_8R_9$ may be provided by the reductive amination of the corresponding keto group $COR_5$, preferably by reaction with the appropriate amine followed by hydrogenation or by reaction with the amine and sodium cyanoborohydride.

(xiii) an alkoxyalkyl group may be provided by the alkylation of the corresponding alcohol, preferably by reaction of the sodium salt of the alcohol with the appropriate alkyl iodide.

(xiv) an alkylthioalkyl group may be provided by the reaction of the corresponding derivatised hydroxyalkyl or haloalkyl group with the appropriate alkylthiol.

An $R_{10}$ hydroxy group in $R_1$ or $R_2$ may be converted to an $R_{10}$ alkoxy group by conventional esterification procedures and an $R_{10}$ hydroxy group may be converted to an $NR_6R_7$ group by condensation with $HNR_6R_7$ in the presence of a dehydrating agent, such as dicyclohexylcarbodiimide.

A $COR_{10}$ group when amide can be converted to a $COR_{10}$ ester group by conventional hydrolysis/esterification in ethanolic HCl. One $COR_{10}$ ester group may be converted to another $COR_{10}$ ester by conventional transesterification procedures. It will be appreciated that when $R_2$ is an ester group, reaction of the compound of formula (VI) with the compound of formula (VII) may also substitute $R_{10}$ in which case subsequent conversion of $R_{10}$ is necessary as described above.

$R_1$ or $R_2$ may be methyl, in which case it may be converted to a $CO_2H$ group by conventional oxidation with an oxidising agent such as potassium permanganate. This conversion is preferably, however, carried out on the intermediate of formula (V) or at an earlier stage.

Conversions of substituents on $R_3$ are generally known in the art of aromatic chemistry. Examples of such conversions are as follows:

(a) an hydroxy group may be converted to acyloxy by conventional acylation procedures, preferably using the acid chloride in pyridine.

(b) a cyano group may be converted to carboxy by base catalysed hydrolysis; preferably using sodium hydroxide in ethanol followed by neutralisation with acid.
(c) an alkoxycarbonyl group may be converted to $CONR_{16}R_{17}$ by heating with the appropriate amine;
(d) a nitro group may be converted to an amino group by reduction, preferably by catalytic reduction using palladium on charcoal;
(e) an amino group may be converted to an alkylamino or acylamino group by conventional amine acylation or alkylation; the acylation is preferably carried out using an acid anhydride and the alkylation using the alkyl halide;

An $R_4$ hydrogen atom may be converted to an $R_4$ $C_{1-6}$ alkyl group by conventional alkylation procedures.

$R_x{'}$ may be hydrogen and converted to $R_x$ halogen by conventional halogenation procedures. For example $R_x{'}$ hydrogen may be converted to $R_x$ bromine by reaction with bromine in methanol at 0° C. Certain $R_x$ groups can be converted to different $R_x$ groups by conventional procedures.

It will be appreciated that these conversions may take place in ay desired or necessary order. Conversions, in particular those involving amine substitution, may also substitute an $R_4$ hydrogen which therefore may need to be protected using an amine protecting group such as 2-methoxy-2-propyl or para-methoxybenzyl, subsequently removed by heating in the presence of an acid such as trifluoroacetic acid.

Pharmaceutically acceptable salts of the compounds of formula (I) may be formed conventionally by reaction with the appropriate acid. Solvates may be formed by crystallization from the appropriate solvent.

Compounds of the formula (VI) are either known compounds or can be prepared by analogy with processes for preparing structurally similar known compounds.

For example, compounds of the formula (VI) wherein Q is chloro may be prepared by the phosphorus oxychloride chlorination of a compound of formula (VIII):

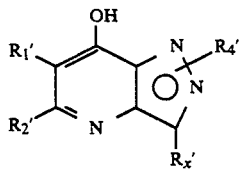

(VIII)

It will be appreciated that the compounds of formula (VIII) wherein $R_4$ is hydrogen exist in the predominant tautomeric form of formula (VIIIa):

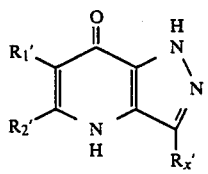

(VIIIa)

Compounds of the formula (VIII) are known compounds or can be prepared by analogy with processes for preparing structurally similar compounds-see for example the references cited above for the compounds of formulae (A) and (B).

As an illustrative procedure, compounds of formula (VIII) in which $R_x{'}$ is lower alkyl, phenyl or substituted phenyl may be prepared by synthesis of an $R_x$-substituted 4-nitropyrazole, followed by catalytic reduction of the corresponding amine and reaction with a β-ketoester toj form a crotonate. Cyclization e.g. using Dowtherm A, gives the compound of formula (VIII) and further reaction with POCl$_3$ the compound of formula (VI).

The following reaction schemes I and II illustrate suitable procedures for compounds in which $R_x$=Me (I) and p-chlorophenyl (II). It will be appreciated that the group $R_4$ can be introduced by conventional alkylation methods, and groups $R_1$, $R_2$ by techniques described above.

SCHEME I

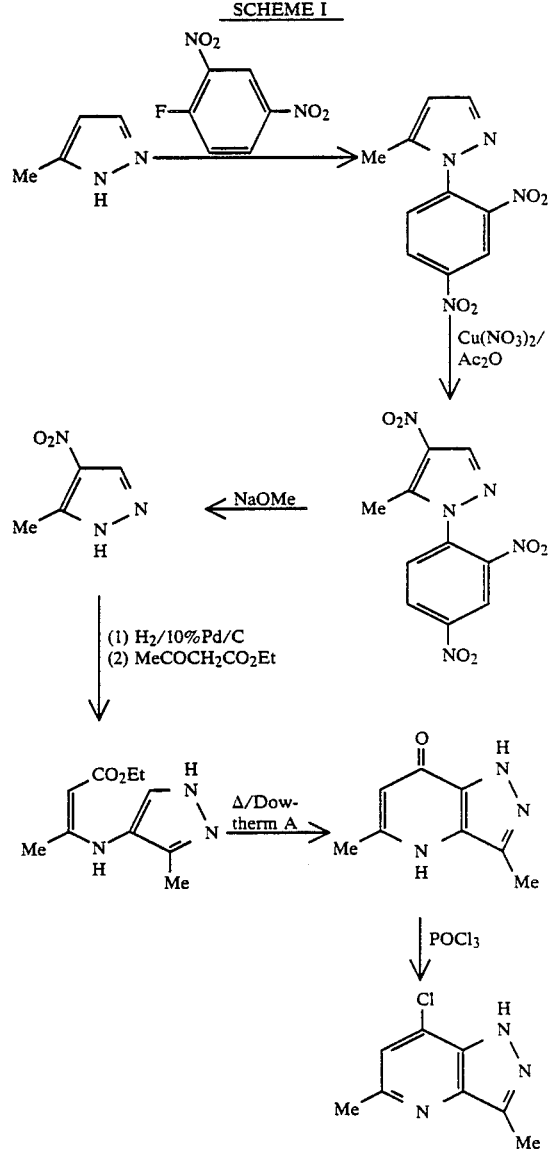

SCHEME II

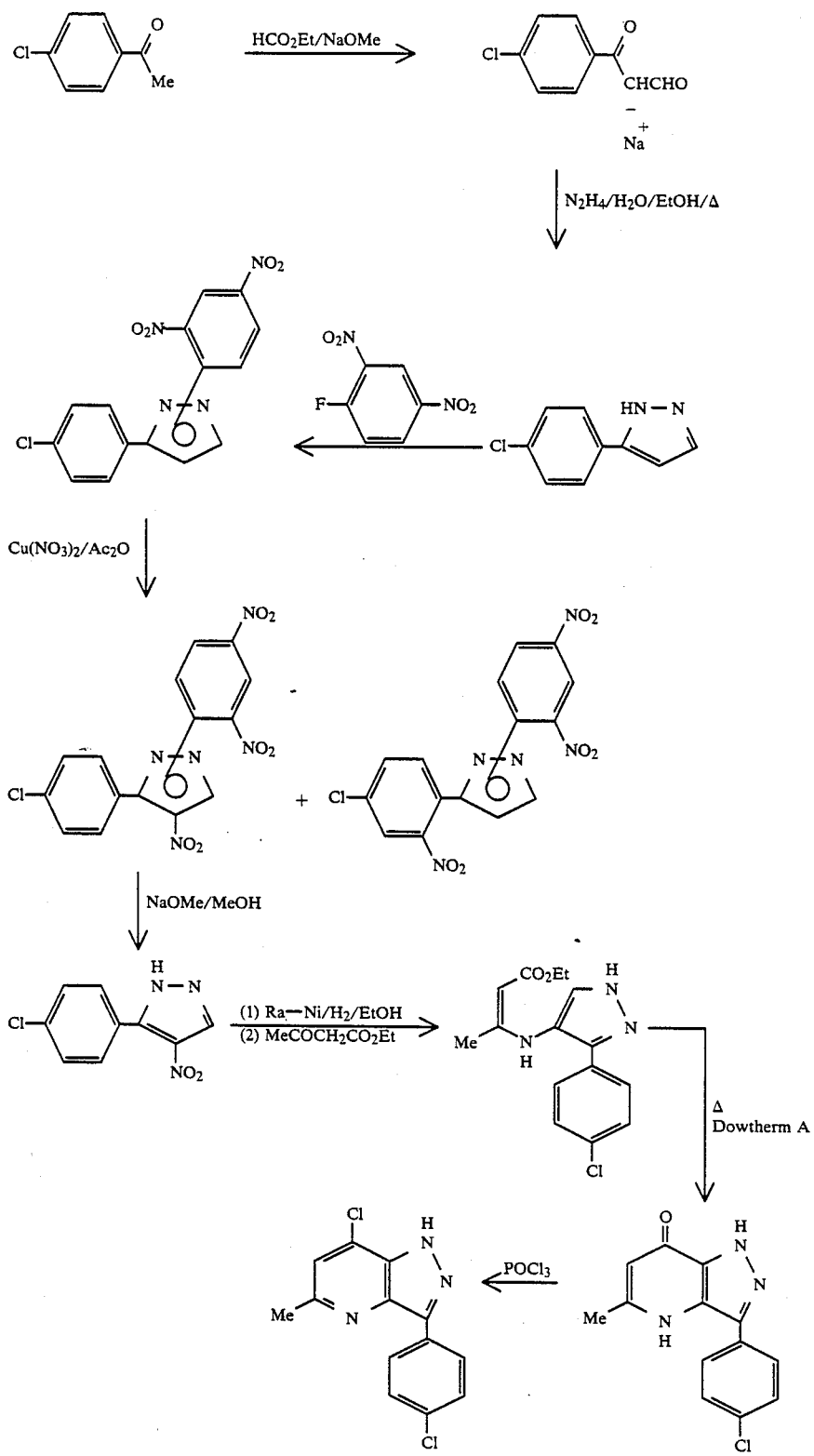

In an alternative procedure illustrated in the following reaction scheme III, an $R_x$ substituent which is phenyl, phenyl substituted by electron donating substituent(s) or other electron-rich ring systems e.g. furyl, pyrryl or thienyl may be introduced into the 3-position of a compound of formula (VI) in which $R_x'$ is hydrogen. Further substituents $R_1'$, $R_2'$, $R_4'$, may be introduced as indicated above.

SCHEME III

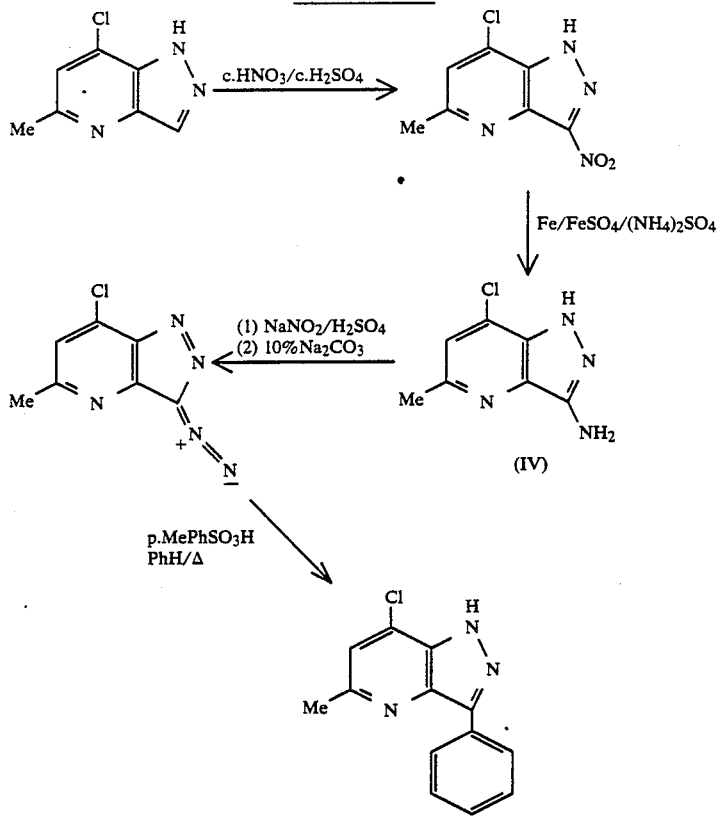

Those intermediates disclosed herein which are novel compounds form an aspect of this invention, together with the disclosed processes for their preparation.

In a further aspect the invention provides a pharmaceutical composition which comprises a compound of formula (I) (as defined above but without the proviso) or a pharmaceutically acceptable salt or solvate thereof and a pharmaceutically acceptable carrier.

The compositions may be adapted for administration via the topical, oral, vaginal, rectal or injection routes. The composition of this invention may be prepared by admixture of the active agent with the carrier and optionally diluents, binders, fillers, disintegrants, flavouring agents, colouring agents, lubricants, preservatives in conventional manner. These conventional excipients may be employed in conventional manner, for example as in the preparation of compositions of ketoprofen, indomethacin, naproxen, acetylsalicylic acid or other anti-inflammatory agents.

The compounds of the invention have topical anti-inflammatory activity and therefore a compound of formula (I) will normally be dispersed in a suitable topically effective vehicle for topical administration to the skin or mucosal membranes.

Cream, lotion, gel, gel stick, ointment, topical solution, douche, wash, spray, or aerosol formulations that may be used as topical vehicles for compounds of the formula (I) are conventional formulations well known in the art, for example, as described in standard text books of pharmaceutics and cosmetics, such as Harry's Cosmeticology published by Leonard Hill Books, Remington's Pharmaceutical Sciences published by Mack Publishing Co., and the British and US Pharmacopoeias. A standard emulsifying ointment base or glycerol or anhydrous polyethylene glycol are simple examples of suitable vehicles. Aqueous solutions or dispersions may be used, for example, as vaginal douches or washes for mouth or throat.

Examples of oils suitable for inclusion in a standard emulsifying ointment base include mineral oils, vegetable oils, synthetic fatty acid esters, fatty alcohols, lanolin and its derivatives.

These compositions will normally include a suitable emulsifier. The composition can range from liquid through semi-liquid to gel types according to the type of emulsion and quantity of any thickening agent which may be present. Examples of emulsifiers include polyhydric alcohol esters such as sorbitan monostearate, fatty acid esters such as glyceryl monostearate, and polyester derivatives of fatty acids or fatty alcohols.

The compositions may also contain anti-oxidants and other conventional ingredients such as preservatives, humectants, perfumes and alcohol. Advantageously, a penetrating agent such as AZONE may also be included.

The compositions for topical treatment may also contain other therapeutic agents such as anti-infective and/or anti-viral agents. Suitable anti-infective agents include the topically applicable antibacterial, anti-yeast, anti-fungal and anti-herpes agents.

These compositions may be used in the topical treatment of atopic, allergic and contact dermatitis, psoriasis, acne, eczema and other inflammatory dermatoses and inflammatory conditions of for example lesions in eyes, ears, nose, throat, vagina and rectum, particularly of the mucosal membranes. Treatment of inflammation of the skin or mucosal membranes may, however, also be carried out utilising an oral composition of the invention, as hereinbefore described.

It will be appreciated that the amount of compound of the formula (I) used will depend on a number of factors such as the nature and severity of the disorder being treated, and the specific compound being used. A typical formulation will suitably contain 0.1 to 20%, more suitably 0.5 to 5% of the compound of formula (I).

A composition of this invention is useful in the treatment of rheumatism and arthritis and in the treatment of pain and other inflammatory conditions and also in the treatment of the prophylaxis of bronchial asthma, rhinitis, hay fever and allergic eczema. Suitably the oral compositions of this invention will be in the form of a unit dose such as a tablet, capsule or reconstitutable powder in a sachet. Such unit doses will generally contain from 10 mg to 1000 mg and more suitably will contain from about 30 mg to 500 mg for example 50 mg to 250 mg of active agent, for example about 50, 100, 150, 200, 250, 300, 350, 400, 450 or 500 mg. These compositions may be administered once or more times a day, for example 2, 3 or 4 times daily, so that the total daily dose for a 70 kg adult will usually be in the range of 20 to 3000 mg and more usually in the range 40 to 1000 mg. Alternatively the unit dose may contain from 2–20 mg of active agent and may be administered in multiples if desired to give the preceeding daily dose.

For use in the treatment or prophylaxis of allergic disorders, in any of the preceding formulations, a suitable dosage unit may contain 0.01 to 500 mg of active ingredient, more suitably 1 to 500 mg for use via the oral route, 0.01 to 10 mg via inhalation, which is preferred. The effective dose of compound depends on the particular compound employed, the condition of the patient and the frequency and route of administration, but in general is in the range of from 0.001 mg/day to 100 mg/day per kilogram of the patient's body weight.

No adverse toxicological effects have been indicated at any of the doses tested.

Where appropriate, small amounts of other anti-asthmatics and bronchodilators, for example sympathomimetic amines such as isoprenaline, isoetharine, salbutamol, phenylephrine and ephedrine; xanthine derivatives such as theophylline and aminophylline and corticosteroids such as prednisolone and adrenal stimulants such as ACTH may be included.

A favoured form of oral composition of this invention is a tablet containing the active agent. The active agent may be in the form of a recompressed granulate of the active ingredient in intimate mixture with a lubricant such as magnesium stearate, a filler such as microcrystalline cellulose and a disintegrant such as sodium starch glycollate.

A particular composition of the invention for inflammatory diseases is a hard gelatin capsule containing the required amount of a compound of the invention in the form of a powder or granulate in intimate mixture with a lubricant, such as magnesium stearate, a filler, such as microcrystalline cellulose, and a disintegrant, such as sodium starch glycollate.

Preparations especially suitable for administration to the respiratory tract include, for example, a snuff, an aerosol, a solution for a nebulizer, or a microfine powder for insufflation, alone or in combination with an inert carrier such as lactose. In such a case the particles of active compound suitably have diameters of less than 50 microns, preferably less than 10 microns.

For parenteral administration, fluid unit dosage forms are prepared utilising a compound of the formula (I) or pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. Parenteral suspensions are prepared in substantially the same manner, except that the compound is suspended in the vehicle instead of being dissolved and sterilised by exposure to ethylene oxide before suspension in a sterile vehicle. Advantageously, a surfactant or wetting agent is included in the composition to facilitate uniform distribution of the compound.

The invention further provides a method of treatment or prophylaxis of inflammatory and/or allergic conditions in mammals including man which comprises the administration of a compound of formula (I) (as defined above but without the proviso) or a pharmaceutically acceptable salt or solvate thereof to the sufferer.

The invention also provides a compound of formula (I) (as defined above but without the proviso) or a pharmaceutically acceptable salt or solvate thereof as an active therapeutic substance for use in treating disorders in mammals, and in particular inflammatory and/or allergic conditions.

Mammals which may be thus treated include humans and domestic or farm animals such as dogs, cats, cattle, sheep or horses.

Most suitably the medicament will be administered orally as 1, 3 or 4 doses per day at the dose level previously indicated.

The following Examples illustrate the invention.

EXAMPLE 1

3-Bromo-7-(2-hydroxyethylamino)-5-methyl-1H-pyrazolo-[4,3-b]pyridine (E1)

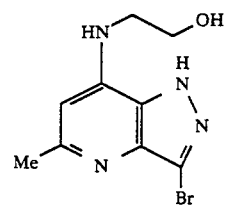

Bromine (4.03 ml of a solution of 0.2 ml bromine in water (5 ml) and methanol (5 ml), equivalent to 0.25 g of bromine) was added dropwise with stirring over a period of ¼ h to an ice-cooled solution of 7-(2-hydroxyethylamino)-5-methyl-1H-pyrazolo[4,3-b]pyridine[1] (300 mg, 0.00156 mole). The resulting pale yellow emulsion was stirred for a further ¾ h at ice-bath temperature and then left to stand at room temperature overnight. The small amount of solid formed was filtered off and the filtrate brought to pH 8 with aqueous ammonia. The resulting white solid was collected, washed with water and dried (222 mg). Purification by chromatography on alumina with initially ethyl acetate and then with a rising percentage of methanol as eluant gave a white solid, m.p. 210°–214° (Found: C, 39.92; H, 4.18; N, 20.53. $C_9H_{11}BrN_4O$ requires C, 39.86; H, 4.08; N, 20.66%).

δ (CDCl₃/DMSO-d₆) 2.66 (3H, s) 3.60–4.10 (4H, overlapping m) 5.80 (1H, brs) 7.99 (1H, s)

Found M⁺270.0114 C₉H₁₁BrN₄O requires 270.0116

1. Patent Application of Beecham Group plc; EP 152-910-A (1984)

DESCRIPTION 1

2-(2,4-Dinitrophenyl)-3-methyl-4-nitropyrazole (D1)

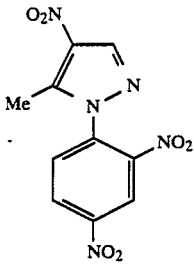

3-Methylpyrazole (8.2 g, 0.1 mole) was protected by treatment with 1-fluoro-2,4-dinitrobenzene (18.6 g, 0.1 mole) and triethylamine (13.13 g, 0.1 mole) which gave the required dinitrophenyl derivative² (90%).

A mixture of copper (II) nitrate trihydrate (20.0 g, 0.082 mole) and acetic anhydride (150 ml) was stirred for 1½ h at room temperature. The 1-(2,4-dinitrophenyl)-3-methyl pyrazole (24 g, 0.1 mole) was then added and the mixture stirred at room temperature for 48 h. A further portion of copper (II) nitrate trihydrate (8.0 g) was added and the reaction mixture stirred for a further 5 h.

Water (200 ml) was added and the reaction mixture stirred overnight. The reaction mixture was adjusted to pH 9–10 with 10% sodium carbonate. The solution was extracted with ethyl acetate (4×250 ml), dried (MgSO₄), filtered and evaporated to dryness to give 2-(2,4-dinitrophenyl)-3-methyl-4-nitro pyrazole as a yellow solid (16.0 g, 55%).

δ (CDCl₃) 2.60 (3H, s) 7.78 (1H, d, J=8 Hz) 8.45–8.60 (2H, m, containing overlapping s) 8.75 (1H, d, J=2 Hz)

2. J. G. Buchanan et al., J. Chem. Soc., Perkin I, 1980, 2567.

DESCRIPTION 2

3-Methyl-4-nitropyrazole (D2)

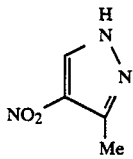

2-(2,4-Dinitrophenyl)-3-methyl-4-nitropyrazole (16.0 g, 0.055 mole) was dissolved in methanol (250 ml). Sodium methoxide (11.0 g, 0.22 mole) was added dropwise as a suspension in methanol. The colour of the reaction mixture changed from yellow to a dark red. The reaction mixture was then stirred at room temperature for 3 h. The methanol was removed in vacuo to give a dark red oil, which was neutralized by pouring onto ice/HCl. The resulting brown precipitate of dinitroanisole was filtered off and discarded. The aqueous filtrate was neutralized with 10% sodium carbonate solution and extracted with ethyl acetate (3×200 ml), dried and evaporated to dryness to give a yellow solid.

Crystallisation from ether/methanol gave pale yellow needles of 3-methyl-4-nitropyrazole (6.0 g, 86%).

δ (CDCl₃) 2.60 (3H, s) 4.30 (1H, brs) 8.05 (1H, s)

DESCRIPTION 3

Ethyl 3-(3-methylpyrazol-4-ylamino) crotonate (D3)

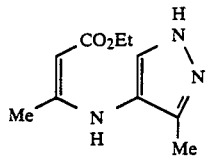

3-Methyl-4-nitropyrazole (6.0 g), 10% palladium-charcoal (0.6 g) and ethanol were shaken with hydrogen until theoretical uptake of hydrogen was complete. The catalyst was filtered off and ethyl acetoacetate (7.8 g, 0.06 mole) added to the ethanol filterate. The ethanol was removed in vacuo and the oily residue heated under nitrogen on a steam bath for 30 minutes. The yellow oil was purified by column chromatography (silica gel eluted with ether/ethyl acetate) to yield the crotonate (7.0 g, 71%) as a pale yellow oil.

δ (CDCl₃) 1.22 (3H, t, J=7 Hz) 1.80 (3H, s) 2.20 (3H, s) 4.10 (1H, brs, exchanges with D₂O) 4.11 (2H, q, J=7 Hz) 4.72 (1H, s) 7.30 (1H, s) 9.55 (1H, s, exchanges with D₂O)

DESCRIPTION 4

4,7-Dihydro-7-oxo-3,5-dimethyl-1H-pyrazolo[4,3-b]pyridine (D4)

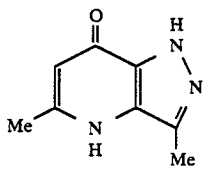

Ethyl 3-(3-methylpyrazole-4-ylamino)crotonate (7.0 g) was dissolved in Dowtherm A (30 ml) and added dropwise under nitrogen to boiling Dowtherm A (120 ml). The mixture was heated under reflux for 45 minutes and then allowed to cool. Petroleum ether (60°–80° C.) (500 ml) was added to the cooled Dowtherm solution and the required pyrazolopyridone precipitated out. The title compound (4.0 g, 74%) was filtered off and washed thoroughly with hot petroleum ether (60°–80° C.). m.p. >346° C. (lit. 346° C.)³.

3. Enrico Ajello, J. Het. Chem., 1971, 8, 1035

DESCRIPTION 5

7-Chloro-3,5-dimethyl-1H-pyrazolo[4,3-b]pyridine (D5)

The pyrazolopyridone (D4) (4.0 g) in phosphoryl chloride (40 ml) was heated at 80°–90° C. for 1 h. The reaction mixture was cooled and the phosphoryl chloride removed under reduced pressure. The residue was poured onto ice and adjusted to pH 8–9 with 10% sodium carbonate solution. The mixture was extracted with hot ethyl acetate (3×150 ml), the combined organic layers dried, filtered and evaporated to dryness to give a beige solid. Crystallisation from ether/pentane gave 7-chloro-3,5-dimethyl-1H-pyrazolo[4,3-b]pyridine (3.4 g, 70%) as a pale beige solid, m.p. 176°–178° C. (lit. 178° C.)[3].

δ (CDCl₃) 2.60 (3H, s) 2.65 (3H, s) 7.13 (1H, s)

EXAMPLE 2

7-(2-Hydroxyethylamino)-3,5-dimethyl-1H-pyrazolo[4,3-b]pyridine (E2)

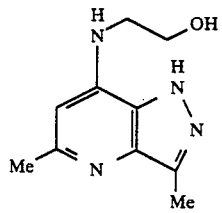

A mixture of ethanolamine (1.0 g, 0.016 mole) and 7-chloro-3,5-dimethyl-1H-pyrazolo[4,3-b]pyridine (1.0 g) in dry xylene (20 ml) was heated under reflux for 48 h. After cooling, the brown oil in the reaction vessel solidified. The solvent was then decanted off and the solid washed several times with xylene. The brown solid was dissolved in aqueous methanol and the pH adjusted to pH 8–9 with 10% sodium carbonate solution. The resulting solid was filtered off, dried and recrystallised from chloroform/methanol to give the title compound as a white solid (0.750 g, 71%), m.p. 225°–230° C. (Found: C, 58.29; H, 6.89; N, 27.06. C₁₀H₁₄N₄O requires C, 58.18; H, 6.84; N, 27.17%).

δ (CDCl₃) 2.42 (3H, s) 2.48 (3H, s) 3.15–3.45 (2H, m) 3.61–3.90 (2H, m) 6.08 (1H, s)

DESCRIPTION 6

7-Chloro-5-methyl-3-nitro-1H-pyrazolo[4,3-b]pyridine (D6)

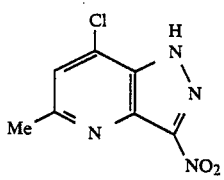

A mixture of concentrated sulphuric acid (8 ml) in concentrated nitric acid (8 ml) was added dropwise with cooling (ice-bath) to a solution of 7-chloro-5-methyl-1H-pyrazolo[4,3-b]pyridine in conc. sulphuric acid (8 ml).

On completing the addition the mixture was stirred in an oil bath at 110°–120° for 3 h. The mixture was poured onto ice and neutralized with 0.880 ammonia. The resulting off-white solid was collected, washed with water repeatedly to remove inorganic salts and dried in vacuo. The bulk of the material had m.p. 255°–260°. A small sample crystallised from water as pale yellow needles, m.p. 270°–274° (dec.).

δ (DMSO-d₆) 2.57 (3H, s) 7.02 (1H, brs) 7.15 (1H, s)

DESCRIPTION 7

3-Amino-7-chloro-5-methyl-1H-pyrazolo[4,3-b]pyridine (D7)

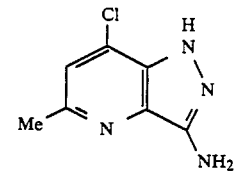

7-Chloro-5-methyl-3-nitro-1H-pyrazolo[4,3-b]pyridine (D6) (0.5 g, 0.0024 mole) was heated at reflux in water (25 ml) with electrolytic iron powder (0.7 g), ferrous sulphate (0.12 g) and ammonium sulphate (0.056 g) for 1 h. Ethanol (13 ml) was then added and heating continued for a further 1 h. The mixture was then filtered while still hot into 5N sulphuric acid (10 ml) to give a yellow solution, which was left to stand at room temperature overnight.

The solution was then diluted with water (25 ml) and brought to pH 9 with 10% sodium hydroxide. The resulting pale yellow precipitate was collected, washed with water and dried. The solid was then taken up in methanol, flocculent material filtered off and the filtrate evaporated to dryness to afford the title compound as a pale yellow solid (318 mg, 74%). A small sample was recrystallised from ethyl acetate/methanol/pentane to give pale yellow crystals, m.p. 196.5–197.5 (Found: C, 44.20; H, 4.09; N, 29.71. C₇H₇N₄Cl.½H₂O requires C, 43.88; H, 4.21; N, 29.24%). Found M+182.0350 C₇H₇N₄Cl requires 182.0359.

δ (CD₃OD) 2.60 (3H, s) 7.20 (1H, s)

DESCRIPTION 8

7-Chloro-3-diazo-5-methyl-pyrazolo[4,3-b]pyridine (D8)

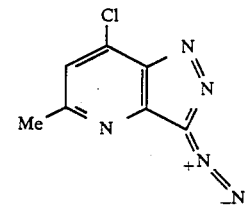

A solution of 3-amino-7-chloro-5-methyl-1H-pyrazolo[4,3-b]pyridine (D7) (0.5 g) in water (13.5 ml) and concentrated sulphuric acid (2 ml) was treated at 0° with a solution of sodium nitrite (0.406 g) in water (2 ml) added dropwise with stirring. On completion of the addition the mixture was stirred at 0° for 20 min before bringing to pH 8 with saturated sodium carbonate. The resulting solid was collected and dried (0.18 g). The filtrate was extracted with chloroform (3×50 ml), the combined extracts dried with magnesium sulphate, filtered and evaporated to dryness to give a yellow solid which was combined with the solid originally collected, m.p. 119°–124° (combined yield 0.5 g). This crude material was recrystallised from cyclohexane to give the title compound as yellow needles (0.358 g, 68%), m.p. 123.5°–125° (decomposition). (Found: C, 43.51; H, 1.88; N, 35.79; Cl, 18.68. C₇H₄ClN₅ requires C, 43.43; H, 2.08;

N, 36.17; Cl, 18.31%). Found M+ 193.0154, C₇H₄ClN₅ requires 193.0155.

δ (CDCl₃) 2.60 (3H, s) 7.13 (1H, s)

DESCRIPTION 9

7-Chloro-5-methyl-3-phenyl-1H-pyrazolo[4,3-b]pyridine (D9)

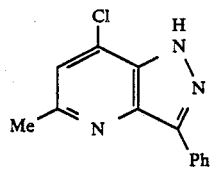

A solution of the diazo compound (D8) (2.45 g) in sodium dried benzene (1 L) with 4-toluenesulphonic acid (2.65 g) was heated at reflux for 7 h and left to stand at room temperature overnight. The solvent was removed under reduced pressure and the dark red residue chromotographed on basic alumina eluting with initially ethyl acetate and then with a rising percentage of methanol. The fractions containing product were combined, evaporated to dryness and recrystallised from methanol/ethyl acetate (5:1) to give the title compound as an off-white crystalline solid (1.74 g, 56%) m.p. 194.5°-197.5°(Found: C, 63.59; H, 3.79; N, 17.44; Cl, 14.48. C₁₃H₁₀N₃Cl requires C, 64.07; H, 4.14; N, 17.24; Cl, 14.55%).

Found M+ 243.0549 C₁₃H₁₀N₃Cl requires 243.0563.

δ (CDCl₃) 2.73 (3H, s) 7.26 (1H, s) 7.30–7.70 (3H, m) 8.40–8.65 (2H, m)

EXAMPLE 3

7-(2-Hydroxyethylamino)-5-methyl-3-phenyl-1H-pyrazolo[4,3-b]pyridine (E3)

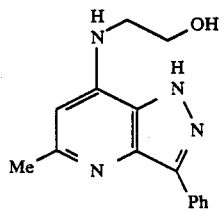

A solution of 7-chloro-5-methyl-3-phenyl-1H-pyrazolo[4,3-b]pyridine (D9) (0.63 g) in xylene (15 ml) with ethanolamine (1.5 ml) was heated at reflux for 3 days under nitrogen. The solvent was then removed under reduced pressure and the residue dissolved in water with the minimum amount of methanol with warming. This solution was brought to pH9 by addition of 10% sodium hydroxide and then further diluted with water. The resulting emulsion was left to stand overnight to give the title compound as a pale yellow crystalline solid which was collected, washed with water and dried under vacuum to afford the title compound (0.686 g, 95%), m.p. softening and partial melting at 135° with resolidification and melting at 186°-188°. (Found: C, 64.58; H, 6.42; N, 20.06. C₁₅H₁₆N₄O.½H₂O requires C, 64.96; H, 6.18; N, 20.20%).

Found M+ 268.1310 C₁₅H₁₆N₄O requires 268.1324.

δ (DMSO-d₆/CDCl₃) 2.56 (3H, s) 3.00–4.00 (4H, multiplets) 4.75 (1H, brt) 6.25 (1H, s) 6.45 (1H, brt) 7.20–7.70 (3H, m) 8.35–8.70 (2H, m) 12.55 (1H, brs)

EXAMPLE 4

7-Allylamino-3,5-dimethyl-1H-pyrazolo[4,3-b]pyridine (E4)

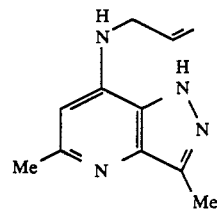

The above compound was prepared from allylamine and 7-chloro-3,5-dimethyl-1H-pyrazolo[4,3-b]pyridine in an analogous manner to the preparation of Example 2 giving a pale yellow solid, m.p. 196°-198°.

δ (CDCl₃) 2.48 (3H, s) 2.51 (3H, s) 3.70–3.80 (2H, m) 4.90–5.25 (2H, m) 5.50–6.00 (1H, m) 6.25 (1H, s)

EXAMPLE 5

7-Allylamino-5-methyl-3-phenyl-1H-pyrazolo[4,3-b]pyridine (E5)

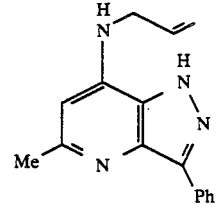

A mixture of 7-chloro-5-methyl-3-phenyl-1H-pyrazolo[4,3-b]pyridine (D9) (1 g), xylene (80 ml) and allylamine (20 ml) was placed in a Parr pressure vessel and heated at 142° rising to 162° for 2 days during which time the internal pressure rose to 75 psi. The vessel was then allowed to cool, the pressure released and the contents evaporated to dryness. The residue was chromatographed on basic alumina eluting with ether and then a rising percentage of methanol (to 25%). Approximately 90% of the starting material was recovered. The fractions containing the required product were combined, evaporated to dryness and recrystallised from ether/pentane with charcoal decolourisation to give the title compound as an off-white crystalline solid, m.p. 92°-105° followed by resolidification and melting 171°-177°.

Found M+ 264.1396 C₁₆H₁₆N₄ requires 264.1375.

δ (CDCl₃) 2.60 (3H, s) 3.70 (2H, d) 5.00–5.25 (2H, m) 5.50 (1H, brs) 5.62–6.83 (1H, m) 6.15 (1H, s) 7.20–7.45 (3H, m) 8.23–8.37 (2H, m)

DESCRIPTION 10

3-(4-Chlorophenyl)-pyrazole hydrochloride (D10)

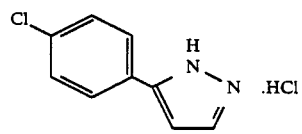

A mixture of 4-chloroacetophenone (70 g) and ethyl formate (34.6 g) was added dropwise to a well stirred mixture of sodium methoxide (27.0 g) in absolute ether (600 ml) keeping the temperature between 0°-10° (cooling in ice). The mixture was stirred for 3 h at this temperature and then left at room temperature overnight.

The product was filtered, washed with ether, and then heated under reflux with hydrazine hydrate (46 g) in ethanol (200 ml) for 30 min. The product was evaporated to dryness in vacuo, and the residue dissolved in excess 5M-hydrochloric acid and extracted with ether. The aqueous layer was basified with 10% sodium carbonate solution and extracted with chloroform (3x). The chloroform layer was washed with water, dried ($Na_2SO_4$), and treated with an excess of ethereal hydrogen chloride. Evaporation to dryness in vacuo followed by trituation with ether afforded the title compound (60 g), m.p. 167°-169° C.

DESCRIPTION 11
3-(4-Chlorophenyl)-1 (or 2)-(2,4-dinitrophenyl)-pyrazole (D11)

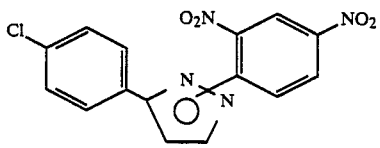

A mixture of 3-(4-chlorophenyl)-pyrazole (D10) (9.6 g), 2,4-dinitrofluorobenzene (10 g) and triethylamine (5.5 g) in toluene (50 ml) was heated under nitrogen under reflux for 18 h. The reaction mixture was cooled, and shaken with an excess of 10% sodium carbonate solution. The resulting precipitate was collected and washed with water (3x), ether (3x) and finally pentane, to afford the title compound (16 g), m.p. 180°-182° C.

DESCRIPTION 12
3-(4-Chlorophenyl)-1 (or -2)-(2,4-dinitrophenyl)-4-nitro-pyrazole (D12)

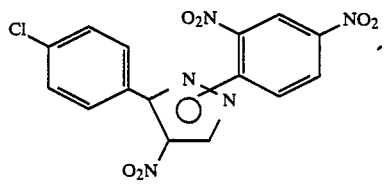

Copper II nitrate trihydrate (10.5 g) was added to acetic anhydride (100 ml) and allowed to stir at room temperature for 1 h. 3-(4-Chlorophenyl)-1 (or -2)-(2,4-dinitrophenyl)-pyrazole (D11) (15 g) was added and the mixture was stirred at room temperature for 4 days. The mixture was treated with an excess of aqueous sodium carbonate and then extracted with chloroform (4×200 ml). The chloroform extract was washed with water, dried ($Na_2SO_4$), evaporated to small volume and chromatographed on silica gel 60 (250 g) using chloroform-pentane (2:1) as the eluant, to afford the title compound (1.1 g), m.p. 140°-142° (ex $CHCl_3$-$Et_2O$). (Found: C, 46.06; H, 1.82; N, 17.91. $C_{15}H_8N_5O_6Cl$ requires C, 46.23; H, 2.06; N, 1797%).

δ ($d_6$-DMSO/$CDCl_3$) 7.45 (2H, d, J=9 Hz) 7.65 (2H, d, J=9 Hz) 8.30 (1H, d, J=10 Hz) 8.75 (2H, m) 9.65 (1H, s)

DESCRIPTION 13
3-(4-Chlorophenyl)-4-nitropyrazole (D13)

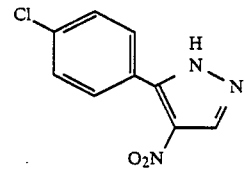

A suspension of 3-(4-chlorophenyl)-1 (or -2)-(2,4-dinitrophenyl)-4-nitro-pyrazole (D12) (1.03 g) in methanol (35 ml) was treated with sodium methoxide (0.153 g) and the mixture was stirred for 30 min at room temperature when all the solid had dissolved. The reaction mixture was evaporated to dryness in vacuo, basified with sodium carbonate solution and extracted with ethyl acetate (3x). The organic layer was washed with water, dried ($Na_2SO_4$) and chromatographed on silica gel 60 (200 g). Elution first with chloroform, and then chloroform-ether (1:1) afforded the title compound (0.6 g) m.p. 172°-174° C. (ex EtOAc-pentane). (Found: C, 47.92; H, 2.48; N, 18.77. $C_9H_6N_3O_2Cl$ requires C, 48.34; H, 2.70; N, 18.79%)

δ ($d_6$-DMSO/$CDCl_3$) 7.50 (2H, d, J=10 Hz) 7.70 (2H, d, J=10 Hz) 8.65 (1H, s)

DESCRIPTION 14
Ethyl 3-[3-(4-chlorophenyl)-pyrazol-4-ylamino]crotonate (D14)

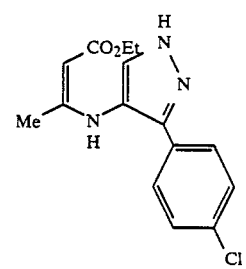

A solution of 3-(4-chlorophenyl)-4-nitropyrazole (D13) (0.5 g) in ethanol (130 ml) was hydrogenated over Raney-nickel (ca. 0.5 g) until uptake of hydrogen ceased (18 h). The mixture was filtered and the filtrate was evaporated to dryness in vacuo and the heated with ethyl acetoacetate (0.34 g) in ethanol (20 ml) under reflux for 5 h. The reaction mixture was chromatographed on silica gel 60 (150 g) eluting first with chloroform pentane (1:1) and later with chloroform to afford the title compound (0.4 g) m.p. 145°-146° C. (ex. ether-pentane). (Found: C, 58.32; H, 5.46; N, 13.52. $C_{15}H_{17}N_3O_2Cl$ requires C, 58.72; H, 5.58; N, 13.69%)

δ ($d_6$-DMSO) 1.40 (3H, t, J=7 Hz) 1.75 (3H, s) 4.10 (2H, q, J=7 Hz) 4.70 (1H, s) 7.50 (2H, d, J=9 Hz) 7.70 (2H, d, J=9 Hz) 9.80 (1H, s) 13.20 (1H, brs)

DESCRIPTION 15

4,7-Dihydro-7-oxo-5-methyl-3-(4-chlorophenyl)-1H-pyrazolo[4,3-b]pyridine (D15)

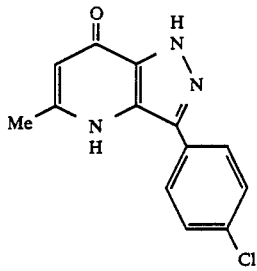

Ethyl 3-[3-(4-chlorophenyl)-pyrazol-4-ylamino]crotonate (D14) (0.6 g) was added to refluxing Dowtherm A (20 ml) under nitrogen and heated for 20 min. The cooled solution was diluted with petroleum ether (40°–60°; 100 ml) and the resulting solid was collected and washed well with petroleum ether to afford the title compound (0.39 g) m.p. 324°–327° C. (Found: C, 60.06; H, 3.74; N, 16.14% $C_{13}H_{10}N_3OCl$ requires C, 60.13; H, 3.88; N, 16.18%)

δ ($d_6$-DMSO) 2.45 (3H, s) 6.00 (1H, brs) 7.55 (2H, d, J=9 Hz) 7.95 (2H, d, J=9 Hz) 11.40 (1H, brs) 13.85 (1H, brs)

Found M+ 261.0465 $C_{13}H_{10}N_3OCl$ requires 261.0484

DESCRIPTION 16

7-Chloro-5-methyl-3-(4-chlorophenyl)-1H-pyrazolo[4,3-b]pyridine (D16)

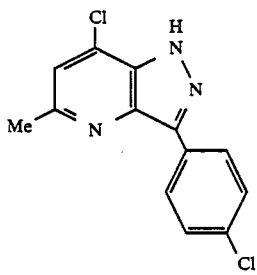

A mixture of 4,7-dihydro-7-oxo-5-methyl-3-(4-chlorophenyl)-1H-pyrazolo[4,3-b]pyridine (D15) (0.8 g) in phosphoryl chloride (20 ml) was heated under reflux under nitrogen for 20 mins and then evaporated to dryness in vacuo. The residue was basified with 10% sodium carbonate solution and extracted with ethyl acetate (3×200 ml). The organic fraction was washed with water, dried ($Na_2SO_4$), and evaporated to dryness in vacuo, and recrystallised from ethyl acetate to afford the title compound (0.4 g), m.p. 243°–245° C.

EXAMPLE 6

3-(4-Chlorophenyl)-7-(2-hydroxyethylamino)-5-methyl-1H-pyrazolo[4,3-b]pyridine (E6)

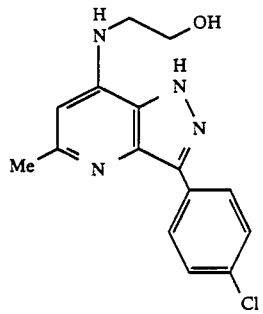

A mixture of ethanolamine (5 ml) and 7-chloro-5-methyl-3-(4-chlorophenyl)-1H-pyrazolo[4,3-b]pyridine (D16) (0.6 g) were heated under reflux in xylene (10 ml) under nitrogen for 48 h. The mixture was evaporated to dryness in vacuo and dissolved in a mixture of water (40 ml) and methanol (60 ml). The pH of the solution was adjusted to ca. 12 with 10% sodium hydroxide solution and then the solution was evaporated to one third volume in vacuo. The resulting precipitate (0.6 g) was collected, washed with water, and recrystallised from ethyl acetate-methanol (trace) to afford the title compound (0.42 g), m.p. 222°–224° C.

EXAMPLE 7

7-Isobutylamino-5-methyl-3-phenyl-1H-pyrazolo[4,3-b]pyridine (E7)

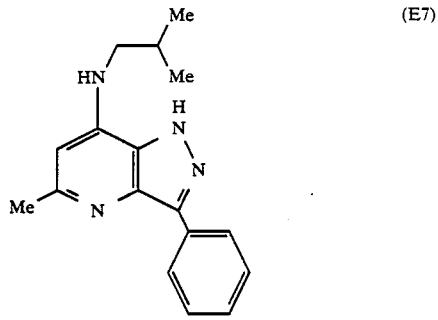

The title compound was prepared using isobutylamine by the method of (E5) as a white solid, m.p. 187°–190°. (Found: C, 72.88; H, 7.19; N, 20.40. $C_{17}H_{20}N_4$ requires C, 72.83; H, 7.19; N, 19.98%)

Found M+ 280.1694 $C_{17}H_{20}N_4$ requires 280.1688

δ (DMSO-$d_6$/$D_2O$) 0.97 (d, 6H, J=7 Hz) 1.60–2.30 (m, 1H) 2.47 (s, 3H) 3.07 (d, 2H, J=7 Hz) 6.30 (s, 1H) 7.20–7.65 (m, 3H) 8.30–8.55 (m, 2H)

DESCRIPTION 17

7-Chloro-5-methyl-3-(methoxyphenyl)-1H-pyrazolo[4,3-b]pyridine (D17)

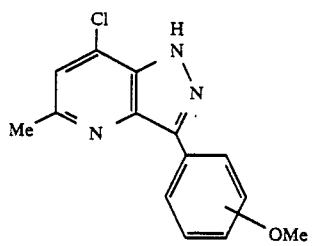

The title compounds (3-isomers) were prepared by the method of (D9) by employing anisole as reaction solvent instead of benzene.

The crude reaction product was purified by chromatography on silica gel with initially 3:1 pentane:ether rising to 1:1 pentane:ether as eluant. A mixture of meta and para isomers in the ratio 1:2 was obtained from the early fractions and pure ortho-methoxy isomer from the later fractions.

7-Chloro-5-methyl-3-[2′-methoxyphenyl]-1H-pyrazolo[4,3-b]pyridine was obtained as a pinkish solid.

δ (CDCl$_3$) 2.72 (s, 3H) 4.07 (s, 3H) 7.00-7.50 (m, 3H) 7.25 (s, 1H) 9.12 (d, 1H) 12.25 (br.s, 1H)

Found M+ 275.0643 C$_{14}$H$_{12}$N$_3$OCl$^{37}$ requires 275.0639 7-Chloro-5-methyl-3-[3′ and 4′-methoxyphenyl]-1H-pyrazolo[4,3-b]pyridines were obtained as a white solid, m.p. 184°–190° after recrystallisation from chloroform/pentane. (Found: C, 61,43; H, 4.44; N, 15.26. C$_{14}$H$_{12}$N$_3$OCl requires C, 61.43; H, 4.42; N, 15.35%)

δ (CDCl$_3$) isomers (p:m=2:1) are quoted separately para-isomer: 2.72 (s, 3H) 3.88 (s, 3H) 7.00-7.08 (m, 2H) 7.23 (s, 1H) 8.40-8.50 (m, 2H) 10.28 (br.s, 1H) meta isomer:

2.73 (s, 3H) 3.92 (s, 3H) 6.92-6.99 (m, 1H) 7.25 (m, 1H) 7.37-7.47 (m, 1H) 8.10-8.18 (m, 2H) 10.28 (br.s, 1H)

EXAMPLE 8

7-(2-Hydroxyethylamino)-5-methyl-3-(methoxyphenyl)-1H-pyrazolo[4,3-b]pyridine (E8)

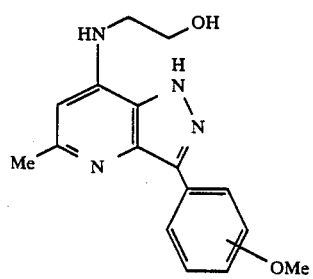

The title compound was prepared form ethanolamine and 7-chloro-5-methyl-3-(methoxyphenyl)-1H-pyrazolo[4,3-b]pyridine (D13) in an analogous manner to the preparation of Example 2 giving a pale yellow solid, m.p. 193°–194° C. Ratio of meta and para isomer 1:2

Found M+ 298.1436. C$_{16}$H$_{18}$N$_4$O$_2$ requires 298.1430.

δ (CD$_3$OD) p-isomer: 2.55 (s, 3H) 3.47-3.55 (m, 2H) 3.83 (s, 3H) 3.81-3.89 (m, 2H) 6.40 (s, 1H) 7.01-7.09 (m, 2H) 8.01-8.09 (m, 2H)

δ (CD$_3$OD) m-isomer: 2.55 (s, 3H) 3.47-3.55 (m, 2H) 3.83 (s, 3H) 3.81-3.89 (m, 2H) 6.02-6.06 (m, 1H) 7.38-7.41 (m, 1H) 7.02-7.08 (m, 2H)

DESCRIPTION 18

7-Chloro-2,3,5-trimethyl-pyrazolo[4,3-b]pyridine (D18)

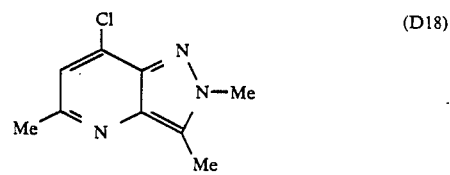

7-Chloro-3,5-dimethyl-1H-pyrazolo[4,3-b]pyridine (900 mg) and dimethylformamide dimethyl acetal (1.06 ml) in dry toluene (10 ml) were heated at reflux for 4 hours. The solvent was removed under reduced pressure and the brown oily residue chromatographed on silica gel eluting with 50:50 ether/pentane to give the title compound (150 mg, 15%).

δ (CDCl$_3$) 2.58 (s, 3H) 2.60 (s, 3H) 4.07 (s, 3H) 7.01 (s, 1H)

This preparation also gave the corresponding 1-methyl compound (50%).

EXAMPLE 9

7-(2-Hydroxyethylamino)-2,3,5-trimethylpyrazolo[4,3-b]pyridine (E9)

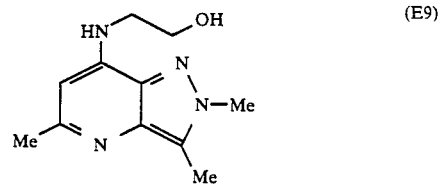

The title compound was prepared from ethanolamine and 7-chloro-2,3,5-trimethylpyrazolo[4,3-b]pyridine in an analogous manner to the preparation of Example 2 giving a white crystalline solid, m.p. 186°–189° C. after recrystallisation from ether/methanol.

Found M+ 220.1326 C$_{11}$H$_{16}$N$_4$O requires 220.1324

δ (CD$_3$OD) 2.45 (s, 3H) 2.58 (s, 3H) 3.50 (t, 2H, J=7 Hz) 3.80 (t, 2H, J=7 Hz) 4.05 (s, 3H) 6.18 (s, 1H)

EXAMPLE 10

7-Amino-3-butyrylamino-5-methyl-1H-pyrazolo[4,3-b]pyridine hydrochloride (E10)

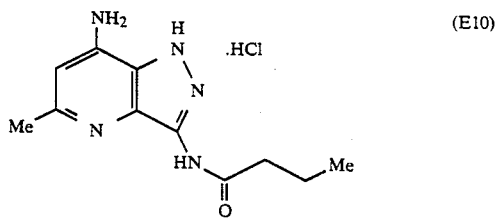

3-Amino-7-chloro-5-methyl-1H-pyrazolo[4,3-b]pyridine (D7) (3.8 g, 0.0208 mole) in dry dioxan (20 ml) and dry pyridine (20 ml) was cooled and butyryl chloride (4.54 g, 2.1 equiv.) in dioxan (15 ml) added dropwise with stirring. On completing the addition the mixture was allowed to warm to room temperature and stirred overnight. Methanol (50 ml) was then added and the mixture stirred for 2 h. Solvents were removed under reduced pressure and a portion of the resulting dark brown oil was stirred in isobutylamine (50 ml) for 2 h. The excess isobutylamine was then evaporated under reduced pressure and the residue triturated with methanol/ethyl acetate. The resulting solid was collected, washed and dried (0.838 g). Further product (1.348 g) was obtained by chromatography of the trituration filtrate (basic alumina with ethylacetate rising to 50% methanol/ethyl acetate as eluant) and crystallisation from methanol. The title compound was obtained as a salmon pink solid, m.p. 294°-8° (decomposition).

(Found: C, 48.58; H, 6.21; N, 25.93; Cl, 12.76. $C_{11}H_{16}N_5OCl$ requires C, 48.98; H, 5.98; N, 25.96; Cl, 13.14%).

Found $M^+$ 233.1275 $C_{11}H_{15}N_5OCl$ requires 233.1277.

$\delta$ (DMSO-$d_6$) 0.93 (t, 3H, J=7 Hz) 1.35–1.90 (m, 2H) 2.30 (t, 2H, J=7 Hz) 2.56 (s, 3H) 6.49 (s, 1H) 8.73 (br.s, 2H) 10.80 (br.s, 1H) 12.90 (br.s, 1H) 14.00 (br.s, 1H)

EXAMPLE 11

7-Amino-3-butyrylamino-5-methyl-1H-pyrazolo[4,3-b]pyridine (E11)

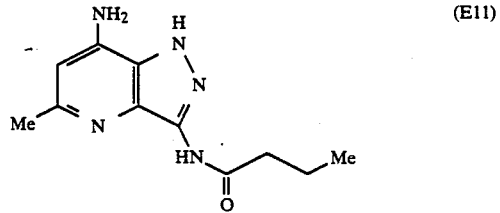

(E11)

7-Amino-3-butyrylamino-5-methyl-1H-pyrazolo[3,4-b]pyridine hydrochloride (E10) (800 mg) was dissolved in aqueous methanol and the pH adjusted to pH 8–9 with 10% sodium carbonate solution. The resulting solid was filtered off, dried and recrystallised from chloroform/methanol to give the title compound as a white solid (80 mg, 12%) m.p. 170°–171° C.

Found $M^+$ 283.1280 $C_{11}H_{15}N_5O$ requires 233.1277

$\delta$ (CD$_3$OD) 1.02 (t, 3H, J=7 Hz) 1.70–1.88 (m, 2H) 2.48 (t, 2H, J=7 Hz) 2.52 (s, 3H) 6.46 (s, 1H)

DESCRIPTION 19

7-Chloro-5-methyl-3-(2- and 3-thienyl)-1H-pyrazolo[4,3-b]pyridine (D19)

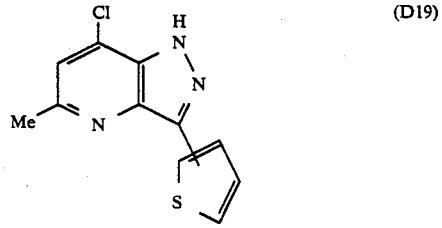

(D19)

A solution of 7-chloro-3-diazo-5-methylpyrazolo[4,3-b]pyridine (420 mg) in thiophene (50 ml) containing 4-toluene sulphonic acid (948 mg) was heated at 80° C. for 1 hour and left to stand at room temperature overnight. The solvent was removed in vacuo and the residual dark brown oil chromatographed on basic alumina with ether as a eluant to give a beige solid which was recrystallised from ether/pentane to give the title compound as a cream coloured solid (250 mg, 58%), m.p. 185°–189° C.

Found $M^+$ 249.0127 $C_{11}H_8N_3ClS$ requires 249.0128

$\delta$ (CDCl$_3$) 2-isomer 2.75 (s, 3H) 7.18 (dd, 1H, J=3.7, 5.0 Hz) 7.25 (s, 1H) 7.38 (dd, 1H, J=1.3, 5.0 Hz) 8.29 (dd, 1H, J=1.3, 3.7 Hz) 10.29 (br.s, 1H)

$\delta$ (CDCl$_3$) 3-isomer 2.75 (s, 3H) 7.25 (s, 1H) 7.40–7.42 (m, 1H) 7.95 (dd, 1H) 8.50 (dd, 1H)

EXAMPLE 12

7-(2-Hydroxyethylamino)-5-methyl-3-(2- and 3-thienyl)-1H-pyrazolo[4,3-b]pyridine (E12)

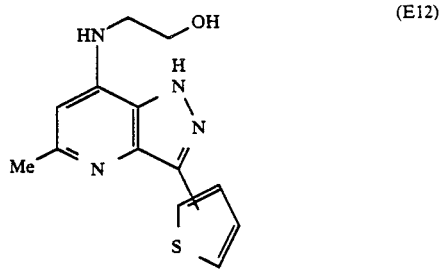

(E12)

7-Chloro-5-methyl-3-(2- and 3-thienyl)-1H-pyrazolo[4,3-b]pyridine (250 mg) and ethanolamine (5 ml) in dry xylene (5 ml) were heated under reflux for 18 h. After cooling the solvent was removed under reduced pressure and the residual oil dissolved in aqueous methanol and adjusted to pH 9 with 10% sodium carbonate solution. The solution was extracted into ethyl acetate (3×50 ml) dried and evaporated to dryness to give an orange oil, which was purified by column chromatography (alumina eluted with 10% methanol/chloroform) to yield the title compound as a beige solid (80 mg), m.p. 194°–197° C. Ratio of 2-thienyl compound to 3-thienyl compound 6:1.

Found $M^+$ 274.0888 $C_{13}H_{14}ON_4S$ requires 274.0887

$\delta$ (CD$_3$OD) 2-isomer 2.55 (s, 3H) 3.45 (t, 2H, J=5 Hz) 3.82 (t, 2H, J=5 Hz) 6.40 (s, 1H) 7.15 (dd, 1H, J=3.6, 4.95 Hz) 7.41 (dd, 1H, J=1.1, 4.95 Hz) 7.95 (dd, 1H, J=1.1, 3.6 Hz)

The structure of this major isomer was confirmed by an NOE difference experiment.

$\delta$ (CD$_3$OD) 3-isomer 2.55 (s, 3H) 3.45 (t, 2H, J=5 Hz) 3.82 (t, 2H, J=5 Hz) 6.40 (s, 1H) 7.50 (dd, 1H, J=2.7, 4.95 Hz) 7.79 (dd, 1H, J=0.9, 4.95 Hz) 8.22 (dd, 1H, J=0.9, 2.7 Hz)

DESCRIPTION 20

Ethyl 3-(3-methyl-2-phenylpyrazol-4-ylamino)crotonate (D20)

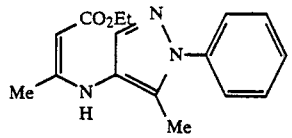

5-Methyl-4-nitro-1-phenylpyrazole[1] (0.200 g) was dissolved in a mixture of water (4 ml) and methanol (6 ml) and then adjusted to pH 7 with 10% sodium carbonate solution. Sodium dithionite (0.52 g) was added portionwise over 1 hour and the temperature of the reaction mixture maintained at 0° C. After the addition was completed the reaction mixture was left stirring at room temperature for 2 hours. The methanol was removed in vacuo and the aqueous slurry extracted into ethyl acetate (3×25 ml), dried (MgSO), filtered and evaporated to dryness to give a yellow oil. Ethyl acetoacetate (2 ml) was added to the oil together with 1 drop of conc. hydrochloric acid and the oily residue heated under nitrogen on a steam bath for 30 min and gave an oily solid which was recrystallised from pentane/ether to give the title compound as a pale yellow solid (0.200 g).

δ (CDCl$_3$) 1.22 (t, 3H, J=7 Hz) 1.81 (s, 3H) 2.21 (s, 3H) 4.10 (q, 2H, J=7 Hz)

7.30–7.35 (m, 5H) 7.40 (s, 1H) 9.70 (s, 1H, exchanges with D$_2$O)

1. I. L. Finar and R. J. Hurlock, J. Chem. Soc., 1958, 3259–3263

DESCRIPTION 21

4,7-Dihydro-7-oxo-3,5-dimethyl-2-phenylpyrazolo[4,3-b]pyridine (D21)

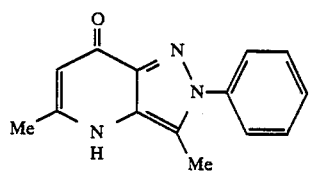

Ethyl 3-(3-methyl-2-phenylpyrazol-4-ylamino)crotonate (0.200 g) was added to boiling Dowtherm A (5 ml) under nitrogen. The mixture was heated under reflux for 30 mins and then allowed to cool. Petroleum ether (60°–80° C.) was added to the cooled Dowtherm solution and the required pyrazolopyridone precipitated out. The title compound (0.120 g) was filtered off and washed thoroughly with hot petroleum ether.

δ (CD$_3$OD) 2.30 (s, 3H) 2.39 (s, 3H) 5.89 (s, 1H) 7.10–7.40 (br.s, 5H)

DESCRIPTION 22

7-Chloro-3,5-dimethyl-2-phenylpyrazolo[4,3-b]pyridine (D22)

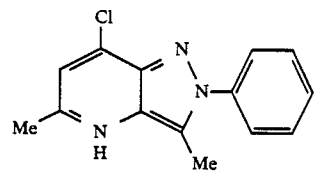

The pyrazolopyridone (D21) (0.12 g) in phosphoryl chloride (5 ml) was heated at 80°–90° C. for 1 H. The reaction mixture was cooled and the phosphoryl chloride removed under reduced pressure. The residue was poured onto ice and adjusted to pH 8–9 with 10% sodium carbonate solution. The mixture was extracted with hot ethyl acetate (3×5 ml), the combined organic layers dried, filtered and evaporated to dryness to give a brown oil which was purified by column chromatography (alumina with ether as eluant) to give a pale yellow solid (0.080 g).

Found M+ 257.0728 C$_{14}$H$_{12}$N$_3$Cl requires 257.0721

EXAMPLE 13

7-(2-Hydroxyethylamino)-3,5-dimethyl-2-phenylpyrazolo[4,3-b]pyridine (E13)

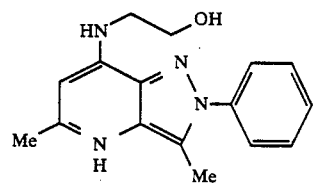

A mixture of ethanolamine (1.0 ml) and 7-chloro-3,5-dimethyl-2-phenylpyrazolo[4,3-b]pyridine (0.080 g) in dry xylene (5 ml) was heated under reflux for 48 h. After cooling, the resulting brown oil solidified. The solvent was decanted off and the solid washed several times with xylene. The brown solid was dissolved in aqueous methanol and the pH adjusted to pH 8–9 with 10% sodium carbonate solution. The resulting solid was filtered off, dried and recrystallised from chloroform/pentane to give the title compound as a beige solid (0.029 g), m.p. 159°–161° C.

Found M+ 282.1482 C$_{26}$H$_{18}$N$_4$O requires 282.1481

δ (CDCl$_3$) 2.55 (s, 3H) 2.60 (s, 3H) 3.55 (t, 2H, J=7 Hz) 3.89 (t, 2H, J=7 Hz) 6.01 (s, 1H) 7.50 (s, 5H)

MOUSE CANTHARIDIN SCREEN

Compounds were tested for topical anti-inflammatory activity in a cantharidin mouse ear screen, modified from Swingle, Reiter and Schwartzmiller [Arch. int. Pharmacodyn. 254, 168–176, 1976].

25 μg cantharidin (in 10 μl THF) was applied to both ears. Compound, in the same solvent, was applied at the same time, to the left ear only. Ears were weighed after 24 hours. Percentage inhibition of the acute inflammatory swelling refers to the increase in weight of left ears (cantharidin plus compound) compared to solvent-treated negative controls, as a proportion of the increase in weight of right ears (cantharidin alone) over similar controls.

| Compound No. | Dose (μg/ear) | % Inhibition |
| --- | --- | --- |
| 2 | 500 | 86*** |
| 3 | 500 | 98*** |
| 4 | 200 | 83*** |
| 5 | 500 | 90*** |
| 6 | 200 | 68** |
| 7 | 500 | 39* |
| 13 | 200 | 43*** |

*$p < 0.05$
**$p < 0.01$
***$p < 0.001$ (Student's 't'-test)

MOUSE OXAZOLONE SCREEN

Compounds were tested for topical anti-inflammatory activity in a screen using the mouse sensitized to oxazolone, by a method modified from that of Dietrich and Hess [Int. Arch. Allergy, 38, 246 (1970)].

Mice were sensitized with oxazolone (2 mg in 20 μl EtOH) on a shaved area of the abdomen. 5 days later, the animals received 10 μl THF/MeOH (1:1 v/v) on the right ear and the test compound in the same solvent on the left ear. 1 hour later, the animals were challenged with 100 μg oxazolone in 10 μl acetone on each ear. Ear weights were measured 24 hours later. Percentage inhibition of the inflammatory swelling refers to the increase in weight of left ears (oxazolone plus compound in THF/MeOH) compared to untreated negative controls, as a proportion of the increase in weight of right ears (oxazolone plus THF/MeOH) only similar controls.

| Compound No. | Dose (μg/ear) | % Inhibition |
| --- | --- | --- |
| 1 | 200 | 22* |
| 2 | 200 | 52* |
| 3 | 500 | 52** |
| 6 | 200 | 31** |

*$p < 0.05$
**$p < 0.01$
***$p < 0.001$ (Student's 't'-test)

We claim:
1. A compound of the formula (I) or a pharmaceutically acceptable salt or solvate thereof:

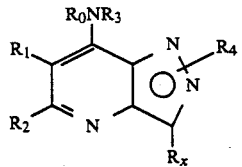

in which:
$R_0$ is hydrogen or $C_{1-6}$ alkyl; or together with $R_3$ is $C_{4-6}$ polymethylene;
$R_1$ and $R_2$ are both hydrogen; or
$R_1$ is hydrogen, $C_{1-6}$ alkyl; and $R_2$ is CN; $CR_5R_6Y$ where $R_5$ and $R_6$ are independently selected from hydrogen and $C_{1-4}$ alkyl and Y is selected from hydrogen, $OR_7$ or $SR_7$ where $R_7$ is hydrogen, $C_{1-4}$ alkyl or $C_{2-4}$ alkanoyl, and $NR_8R_9$ where $R_8$ and $R_9$ are independently hydrogen, $C_{1-4}$ alkyl, $C_{2-4}$ alkenyl or $C_{2-4}$ alkanoyl or together are $C_{4-6}$ polymethylene; or $COR_{10}$ where $R_{10}$ is OH or $C_{1-4}$ alkyl, or $COR_{10}$ is a pharmaceutically acceptable ester or amide where $R_{10}$ is $C_{1-6}$ alkoxy, $C_{2-6}$ alkenyloxy, phenoxy or benzyloxy where the phenyl/benzyl ring is optionally substituted by one or two of halogen, $CF_3$, $C_{1-4}$ alkoxy and $C_{1-4}$ alkyl or $R_{10}$ is $NR_{20}R_{21}$ where $R_{20}$ and $R_{21}$ are independently hydrogen, $C_{1-6}$ alkyl, $C_{2-6}$ alkenyl, benzyl or phenyl optionally substituted by one or two or halogen, $CF_3$, $C_{1-4}$ alkoxy and $C_{1-4}$ alkyl, or
$R_2$ is hydrogen, $C_{1-6}$ alkyl, or phenyl optionally substituted by halogen, $CF_3$, $C_{1-4}$ alkoxy or $C_{1-4}$ alkyl; and $R_1$ is CN, $CR_5R_6Y$ or $COR_{10}$ as defined for $R_2$ above; or
$R_1$ and $R_2$ together form $C_3$–$C_6$ polymethylene optionally substituted by $C_1$–$C_4$ alkyl;
$R_3$ is hydrogen; or $C_{1-10}$ alkyl or $C_{3-10}$ cycloalkyl, either optionally substituted by hydroxy, $C_{1-14}$ alkoxy, thiol, $C_{1-4}$ alkylthio or $NR_{11}R_{12}$ wherein $R_{11}$ and $R_{12}$ are independently hydrogen, $C_{1-6}$ alkyl or $C_{2-7}$ alkanoyl or together are $C_{3-6}$ polymethylene; $C_{2-10}$ alkenyl; or phenyl optionally substituted by one or two of halogen, $CF_3$, $C_{1-4}$ alkoxy, $C_{1-4}$ alkyl, hydroxy, nitro, cyano, $C_{2-10}$ acyloxy, $NR_{13}R_{14}$ wherein $R_{13}$ and $R_{14}$ are independently selected from hydrogen, $C_{1-6}$ alkyl, or $C_{2-7}$ alkanoyl; or $COR_{15}$ wherein $R_{15}$ is hydroxy, $C_{1-6}$ alkoxy or $NR_{16}R_{17}$ wherein $R_{16}$ and $R_{17}$ are independently selected from hydrogen or $C_{1-6}$ alkyl; or
$R_3$ is furyl, thienyl, pyrryl, benzofuranyl, benzothienyl or indolyl, optionally substituted by one or two substituents selected from halogen, $CF_3$, $C_{1-4}$ alkoxy, $C_{1-4}$ alkyl, hydroxy, nitro, cyano, $C_{2-10}$ acyloxy, $NR_{23}R_{24}$ wherein $R_{23}$ and $R_{24}$ are independently selected from hydrogen, $C_{1-6}$ alkyl, $C_{2-7}$ alkanoyl or $C_{1-6}$ alkylsulphonyl; or $COR_{25}$ wherein $R_{25}$ is hydroxy, $C_{1-6}$ alkoxy or $NR_{26}R_{27}$ wherein $R_{26}$ and $R_{27}$ are independently selected from hydrogen or $C_{1-6}$ alkyl;
$R_4$ is hydrogen; or $C_{1-4}$ alkyl, phenyl or benzyl, each of which is optionally substituted in the phenyl ring by one or two of halogen, $CF_3$, $C_{1-4}$ alkoxy or $C_{1-4}$ alkyl and is attached at nitrogen atom 1 or 2; and
$R_x$ is halogen, nitro, $NR_{18}R_{19}$ where $R_{18}$ and $R_{19}$ are independently hydrogen, $C_{1-6}$ alkyl or $C_{2-7}$ alkanoyl, nitrile, COOH, CONH$_2$, phenyl or benzyl optionally substituted by one or two of halogen, nitro, $C_{1-6}$ alkoxy, hydroxy, $C_{2-7}$ alkanoyloxy, $NR_{18}R_{19}$, $C_{1-6}$ alkyl, $CF_3$, CN; thienyl, furyl or pyrryl optionally N-substituted by $C_{1-6}$ alkyl.

2. A compound according to claim 1 in which $R_3$ is hydrogen; methyl, ethyl, n- or iso-propyl, n-, iso- sec- or tert-butyl, n-pentyl, $(CH_2)_nCH_3$ wherein n is 5 to 7, or cyclohexyl, optionally substituted by hydroxy, methoxy, n- or iso-propoxy, thiol, methylthio or amino optionally substituted by one or two methyl or acetyl groups or by $C_4$ or $C_5$ polymethylene; prop-1-enyl, prop-2-enyl, 1-methylvinyl, but-1-enyl, but-2-enyl, but-3-enyl, 1-methylenepropyl, 1-methylprop-1-enyl and 1-methylprop-2-enyl in their E and Z forms where stereoisomerism exists; or phenyl optionally substituted by one or two chloro, bromo, methoxy, ethoxy, n- and iso-propoxy, methyl, ethyl, n- and iso-propyl, n-, iso-, sec- and tert-butyl, hydroxy, nitro, cyano, acetoxy, propionyloxy, benzyloxy, $NR_{13}^1R_{14}^1$ wherein $R_{13}^1$ and $R_{14}^1$ are independently selected from hydrogen, methyl, ethyl, n- and iso-propyl, acetyl, and propionyl; $COR_{15}^1$ wherein $R_{15}^1$ is hydroxy, methoxy, ethoxy or $NR_{16}^1R_{17}^1$ wherein $R_{16}^1$ and $R_{17}^1$ are independently selected from hydrogen, methyl, n- and iso-propyl.

3. A compound according to claim 2 in which $R_3$ is, 2-methylallyl, 2-hydroxyethyl, 3-hydroxypropyl, 2- dimethylaminoethyl, 3-dimethylaminopropyl, 3-diethylaminopropyl, phenyl and phenyl substituted by one of hydroxy, nitro, cyano, carboxy, t-butyl and ethoxycarbonyl in the 3- or 4-position.

4. A compound according to claim 1, in which $R_x$ is chloro, bromo, thienyl, phenyl optionally substituted with chloro, hydroxy or methoxy; or a group NR-$R_{19}$ where $R_{19}$ is $C_{2-7}$ alkanoyl.

5. A compound according to claim 1, in which $R_1$ is hydrogen and $R_2$ is $C_{1-6}$ alkyl.

6. A compound according to claim 1 in which $R_o$ is hydrogen.

7. A compound selected from the group consisting of:
3-Bromo-7-(2-hydroxyethylamino)-5-methyl-1H-pyrazolo[4,3-b]pyridine,
7-(2-Hydroxyethylamino)-5-methyl-3-phenyl-1H-pyrazolo[4,3-b]pyridine,
7-Allylamino-5-methyl-3-phenyl-1H-pyrazolo[4,3-b]pyridine,
3-(4-Chlorophenyl)-7-(2-hydroxyethylamino)-5-methyl-1H-pyrzolo[4,3-b]pyridine,
7-Isobutylamino-5-methyl-3-phenyl-1H-pyrazolo[4,3-b]pyridine,
7-(2-Hydroxyethylamino)-5-methyl-3-(methoxyphenyl)-1H-pyrazolo[4,3-b]pyridine,
7-Amino-3-butyrylamino-5-methyl-1H-pyrazolo[4,3-b]pyridine hydrochloride,
7-Amino-3-butyrylamino-5-methyl-1H-pyrazolo[4,3-b]pyridine,
7-(2-Hydroxyethylamino)-5-methyl-3-(2- and 3-thienyl)-1H-pyrazolo[4,3-b]pyridine.

8. A pharmaceutical composition for the treatment of disorders relating to inflammatory and/or allergic conditions comprising a pharmaceutically effective amount of a compound according to claim 1, and a pharmaceutically acceptable carrier.

9. A composition according to claim 8 in unit dosage form.

10. A method of treating inflammation or allergic conditions in mammals which comprises administering an effective, non toxic amount of a compound according to claim 1 to a sufferer.

* * * * *

UNITED STATES PATENT AND TRADEMARK OFFICE
CERTIFICATE OF CORRECTION

PATENT NO. :  4,833,136

DATED     :  May 23, 1989

INVENTOR(S) :  Markwell et al.

It is certified that error appears in the above-identified patent and that said Letters Patent is hereby corrected as shown below:

Title page, Abstract, right column, fifth line from bottom of page, "optinoally" should read
-- optionally --;

Column 4, formula (V) should appear as follows:

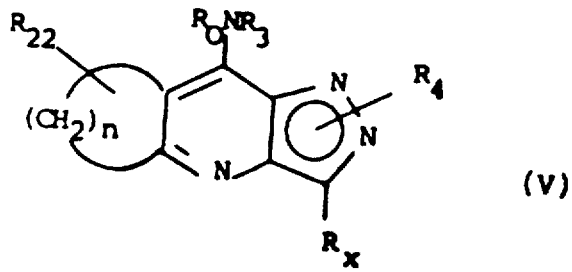

Column 4, line 60, "q" should read -- Q --;

Column 7, line 26, "ay" should read -- any --;

Column 8, line 10, "toj" should read -- to --;

Column 15, lines 27-28, "1-(2,4-dinitrop henyl)" should read -- 1-(2,4-dinitrophenyl) --;

UNITED STATES PATENT AND TRADEMARK OFFICE
CERTIFICATE OF CORRECTION

PATENT NO.  : 4,833,136                              Page 2 of 2
DATED       : May 23, 1989
INVENTOR(S) : Markwell et al.

It is certified that error appears in the above-identified patent and that said Letters Patent is hereby corrected as shown below:

Column 19, line 23, "witha" should read -- with a --;

Column 29, line 26, "(MgSO)" should read --(MgSO$_4$)--;

Column 32, line 13, claim 1, "$C_{1-14}$" should read -- $C_{1-4}$ --;

Column 32, line 48, claim 2, "iso- sec-" should read -- iso-, sec- --;

Column 33, line 7, claim 4, "NR-$R_{19}$" should read -- NH-$R_{19}$ --;

Column 33, line 22, claim 7, "pyrzolo" should read -- pyrazolo --.

Signed and Sealed this

Twenty-ninth Day of October, 1991

Attest:

HARRY F. MANBECK, JR.

*Attesting Officer*   *Commissioner of Patents and Trademarks*